(12) United States Patent
Beam et al.

(10) Patent No.: US 10,457,976 B2
(45) Date of Patent: Oct. 29, 2019

(54) PREPARING ANTIBODIES FROM CHO CELL CULTURES FOR CONJUGATION

(71) Applicant: SEATTLE GENETICS, INC., Bothell, WA (US)

(72) Inventors: Kevin Beam, Monroe, WA (US); Damon Meyer, Bellevue, WA (US); Bradley Hayes, San Diego, CA (US); Robert Lyon, Sammamish, WA (US); John Valliere-Douglass, Seattle, WA (US)

(73) Assignee: Seattle Genetics, Inc., Bothell, WA (US)

( * ) Notice: Subject to any disclaimer, the term of this patent is extended or adjusted under 35 U.S.C. 154(b) by 50 days.

(21) Appl. No.: 15/039,179

(22) PCT Filed: Nov. 21, 2014

(86) PCT No.: PCT/US2014/066889
§ 371 (c)(1),
(2) Date: May 25, 2016

(87) PCT Pub. No.: WO2015/077605
PCT Pub. Date: May 28, 2015

(65) Prior Publication Data
US 2017/0159099 A1 Jun. 8, 2017

Related U.S. Application Data

(60) Provisional application No. 61/908,568, filed on Nov. 25, 2013.

(51) Int. Cl.
| | |
|---|---|
| *C12Q 1/26* | (2006.01) |
| *A61K 47/68* | (2017.01) |
| *C12N 9/00* | (2006.01) |
| *C12P 21/00* | (2006.01) |
| *C12N 5/00* | (2006.01) |
| *C07K 1/107* | (2006.01) |
| *C07K 16/00* | (2006.01) |
| *C12N 5/071* | (2010.01) |
| *C12N 9/02* | (2006.01) |

(52) U.S. Cl.
CPC ............... *C12Q 1/26* (2013.01); *A61K 47/68* (2017.08); *C07K 1/1077* (2013.01); *C07K 16/00* (2013.01); *C12N 5/0682* (2013.01); *C12P 21/00* (2013.01); *C07K 2317/14* (2013.01); *C07K 2319/00* (2013.01); *C12N 9/0051* (2013.01)

(58) Field of Classification Search
CPC ........ C12Q 1/26; A61K 47/68; C07K 1/1077; C07K 16/00; C07K 2317/14; C07K 2319/00; C12N 5/0682; C12N 9/0051; C12P 21/00

See application file for complete search history.

(56) References Cited

U.S. PATENT DOCUMENTS

| | | | |
|---|---|---|---|
| 4,880,935 | A | 11/1989 | Thorpe |
| 5,122,368 | A | 6/1992 | Greenfield et al. |
| 5,622,929 | A | 4/1997 | Willner et al. |
| 5,824,805 | A | 10/1998 | King et al. |
| 6,214,345 | B1 | 4/2001 | Firestone et al. |
| 7,498,298 | B2 | 3/2009 | Doronina et al. |
| 7,659,241 | B2 | 2/2010 | Senter et al. |
| 2013/0309223 | A1 | 11/2013 | Sutherland et al. |

FOREIGN PATENT DOCUMENTS

| | | |
|---|---|---|
| WO | WO2006/083971 A2 | 8/2006 |
| WO | WO2006/083971 A3 | 8/2006 |
| WO | WO2007109163 * | 9/2007 |
| WO | WO2009/058812 A1 | 5/2009 |
| WO | WO2010/114312 A2 | 10/2010 |
| WO | WO2010/114312 A3 | 10/2010 |
| WO | 2011/130613 A1 | 10/2011 |
| WO | 2013/132495 A1 | 9/2013 |
| WO | WO2013/173496 A2 | 11/2013 |
| WO | WO2013/173496 A3 | 11/2013 |

OTHER PUBLICATIONS

Benayoun et al., J Biol Chem 276(17): 13830-13837.*
Daithankar et al., Biochemistry 51: 265-272, 2012.*
Munday et al., Free Radical Biology & Med 36(6): 757-764, 2004.*
De Andrade et al., In Vitro In Vitro Cell.Dev.Biol.—Animal (2011) 47:716-727, 2011.*
Kaneko et al., Journal of Bioscience and Bioengineering vol. 109 No. 3, 274-280, 2010.*
Lyon et al., Methods in Enzymology 502: 123-138, 2012.*
Saito et al., Advanced Drug Delivery Reviews 55: 199-215, 2003.*
Liu et al., MAbs 2(5):480-99. Epub 2010 Sep. 1, 2010.*
Grossman, et al., "An Inhibitory Antibody Blocks the First Step in the Dithiol/Disulfide Relay Mechanism of the Enzyme QSOX1", J. Mol. Biol., vol. 425, No. 22, pp. 4366-4378, (2013).
Hogwood, et al., "The Dynamics of the CHO Host Cell Protein Profile During Clarification and Protein A Capture in a Platform Antibody Purification Process", Biotechnology and Bioengineering, vol. 110, No. 1, pp. 240-251, (Jan. 2013)
Joucla, G. et al "Cation exchange versus multimodal cation exchange resins for antibody capture from CHO supernatants: Identification of contaminating Host Cell Proteins by mass spectrometry" Journal of Chromatography B 942-943 (2013) 126-133.

(Continued)

*Primary Examiner* — Phuong Huynh
(74) *Attorney, Agent, or Firm* — Seattle Genetics, Inc.

(57) ABSTRACT

The invention is based in part on the observation that a CHO cell oxidizing enzyme, particularly QSOX1, can survive a seemingly rigorous antibody purification process to reduce subsequent conjugation efficiency of the antibody to a drug. Whether the oxidizing enzyme survives the purification procedure depends on which purification techniques are employed which can vary from one antibody to another. With knowledge that contamination with a CHO cell oxidizing enzyme is a potential problem for subsequent conjugation, a suitable purification scheme can be devised for any antibody that eliminates or at least reduces CHO oxidizing enzyme(s) to an acceptable level.

20 Claims, 6 Drawing Sheets

Specification includes a Sequence Listing.

(56) References Cited

OTHER PUBLICATIONS

Liu, Hui F. et al "Recovery and purification process development for monoclonal antibody production" MAbs, (2010) vol. 2, No. 5, 480-499.
XP_003500174, Predicted: sulfhydryl oxidase 1 [Cricetulus griseus] (Oct. 26, 2011).
XP_007639037, Predicted: sulfhydryl oxidase 1 isoform X1 [Cricetulus griseus] (May 27, 2016).
Accession No. UniProtKB/Swiss-Prot: Q6ZRP7.3, RecName: Full=Sulfhydryl oxidase 2; AltName: Full=Neuroblastoma-derived sulfhydryl oxidase; AltName: Full=Quiescin Q6-like protein 1; Flags: Precursor (Jul. 6, 2016).
Accession No. O00391, UniProtKB, QSOX1_HUMAN (Sep. 19, 2006).
Sledziecka, Anna Katarzyna "Characterization of Oxidase Activity Responsible for Catalyzing Covalent Lipoprotein (a) Assembly" Covalent Lipoprotein (A) Assembly (2008).
PCT Application No. PCT/US14/66889, Search Report and Written Opinion dated Mar. 10, 2015, 13 pages.
PCT Application No. PCT/US14/66889, International Preliminary Report on Patentability dated May 31, 2016, 9 pages.
Dubowchik et al., "Receptor-mediated and enzyme-dependent targeting of cytotoxic anticancer drugs", Pharmacology & Therapeutics 83:67-123, (1999).
Johnson et al., "Anti-Tumor Activity of CC49-Doxorubicin Immunoconjugates", Anticancer Research 15: 1387-1394, (1995).
Lau et al., "Novel Doxorubicin-Monoclonal Anti-carcinoembryonic Antigen Antibody Immunoconjugate Activity in vitro", Bioorganic & Medicinal Chemistry. vol. 3, No. 10, pp. 1305-1312, (1995).
Neville et al., "Enhancement of Immunotoxin Efficacy by Acid-cleavable Cross-linking Agents Utilizing Diphtheria Toxin and Toxin Mutants", The Journal of Biological Chemistry, vol. 264, No. 25, pp. 14953-14661, (Sep. 5, 1989).
Thorpe et al., "New Coupling Agents for the Synthesis of Immunotoxins Containing a Hindered Disulfide Bond with Improved Stability in Vivo", Cancer Research 47, pp. 5924-5931, (Nov. 15, 1987).
Wawrzynczak et al., "Methods for preparing immunotoxins: Effect of the linkage on activity and stability", Immunoconjugates: Antibody Conjugates in Radioimagery and Therapy of Cancer, Oxford UniversityPress, pp. 28-55, (1987).
Payne, "Progress in immunoconjugate cancer therapeutics", Cancer Cell, vol. 3, pp. 207-212, (Mar. 2003).
Rudolf, et al., "Proteolytic processing of QSOX1A ensures efficient secretion of potent disulfide catalyst", Biochem. J., vol. 454, pp. 181-190, (May 2013).
Author Unknown, "Phenyl Membrane Adsorber for Bioprocessing", sartorious stedim biotech, available at: http://www.sartorius.de/mediafile/Appl_Sartobind_Phenyl_Membrane_Adsorber_SL-4048-e.pdf, 6 pages, (2008).
Author Unknown, "Two-step purification of monoclonal $IgG_1$ from CHO cell culture supernatant" GE Healthcare Life Sciences, Application Note 28-9078-92 AD, 6 pages, (2011).

* cited by examiner

PREPARING ANTIBODIES FROM CHO CELL CULTURES FOR CONJUGATION

This application is a US national stage filing under 35 U.S.C. 371 of International Application No. PCT/US2014/066889, filed Nov. 21, 2014, which claims the benefit of U.S. Provisional Application No. 61/908,568, filed Nov. 25, 2013, both of which are incorporated herein by reference in their entirety.

REFERENCE TO A SEQUENCE LISTING

This application includes an electronic sequence listing in a file named 3100-00111US_ST25.txt created on Aug. 7, 2018 and containing 157 KB, which is hereby incorporated by reference in its entirety for all purposes.

BACKGROUND

After hundreds of clinical trials, about thirty monoclonal antibodies have been approved by the FDA to-date for treating a variety of indications including cancer, autoimmune disease and infectious agents. One reason that more antibodies have not been approved is that mechanisms of action provided by an antibody alone, such as effector function or blocking receptor-ligand interactions may not be sufficiently powerful to have a substantial therapeutic effect. Antibody-drug conjugates (ADCs) provide additional mechanisms, particularly delivery of a toxic moiety coupled to the antibody to the interior of a cell, thereby killing the cell or otherwise inhibiting its proliferation. Currently two ADCs are marketed: brentuximab vedotin and trastuzumab emtansine. Many other ADCs are at various stages of development. Production of ADC's involves antibody expression and purification, followed by chemical conjugation of the antibody to a drug usually via a linker.

DEFINITIONS

Figure 1:
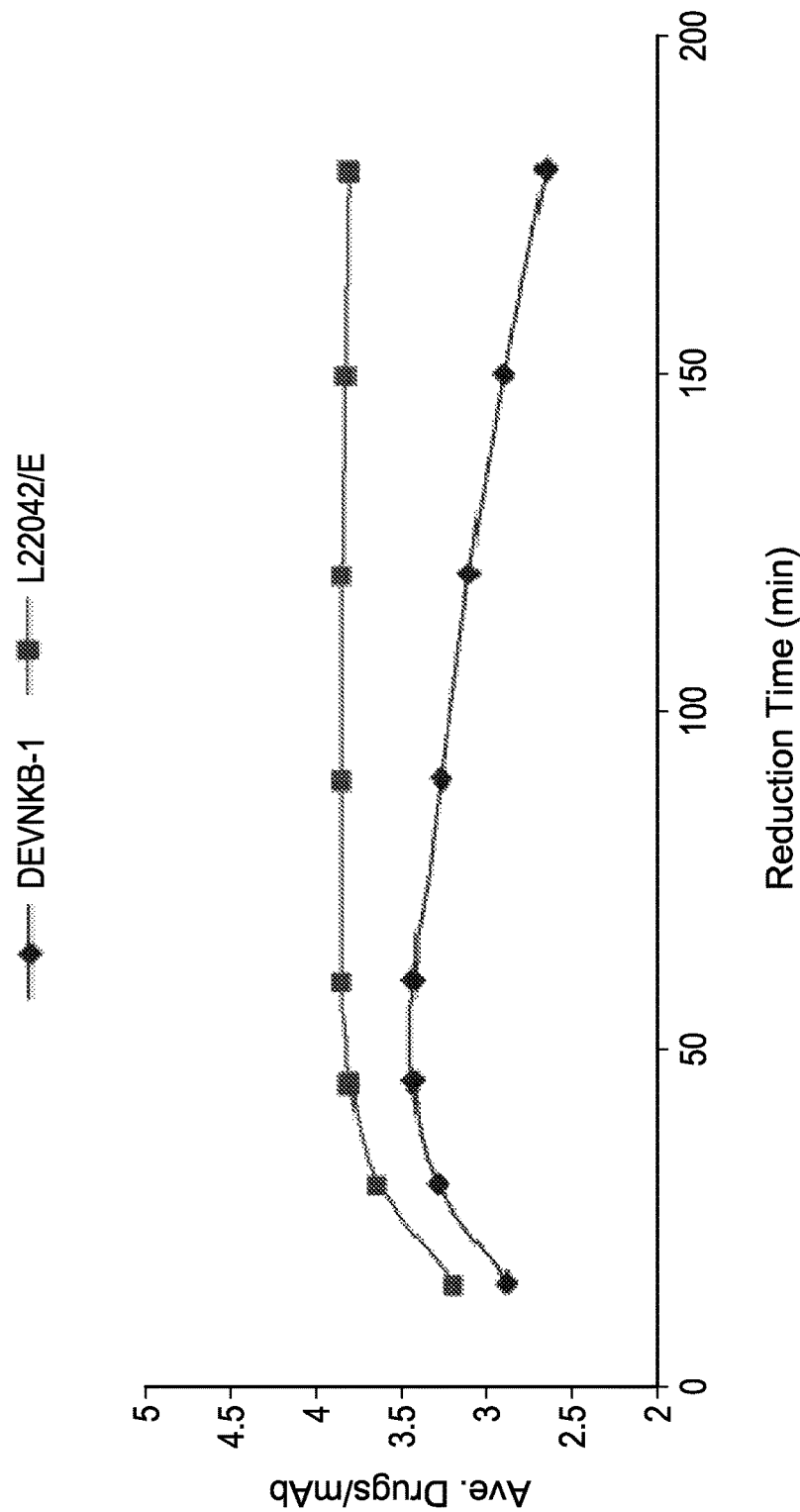
FIG. 1: Impact of oxidizing impurity on drug load. Samples were reduced and conjugated at the times indicated. The trend in which the conjugation level decreases with time indicates the presence of an oxidizing impurity.

An isolated antibody or ADC is typically at least 50% w/w pure of interfering proteins and other contaminants arising from its production or purification but does not exclude the possibility that the monoclonal antibody is combined with an excess of pharmaceutical acceptable carrier(s) or other vehicle intended to facilitate its use. Sometimes monoclonal antibodies or ADCs are at least 60%, 70%, 80%, 90%, 95 or 99% w/w pure of interfering proteins and contaminants from production or purification.

Specific binding of a monoclonal antibody alone or as a component of an ADC to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The basic antibody structural unit is a tetramer of subunits. Each tetramer includes two pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region is a light chain variable region without the light chain signal peptide. The carboxy-terminal portion of each chain defines a constant region. The heavy chain constant region is primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, antibody fragments compete with the intact antibody from which they were derived for specific binding to the target including separate heavy chains, light chains Fab, Fab', F(ab')$_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$-$V_H$-$C_H$3), a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)). The term "antibody" includes an antibody by itself (naked antibody) or an antibody conjugated to a cytotoxic or cytostatic drug.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range.

An antibody effector function refers to a function contributed by an Fc domain(s) of an Ig. Such functions can be, for example, antibody-dependent cellular cytotoxicity, antibody-dependent cellular phagocytosis or complement-dependent cytotoxicity. Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by $CD16^+$ effector cells through the secretion of membrane pore-forming proteins and proteases, while phagocytosis is mediated by $CD32^+$ and $CD64^+$ effector cells (see *Fundamental Immunology*, $4^{th}$ ed., Paul ed., Lippincott-Raven, N.Y., 1997, Chapters 3, 17 and 30; Uchida et al., 2004, *J. Exp. Med.* 199:1659-69; Akewanlop et al., 2001, *Cancer Res.* 61:4061-65; Watanabe et al., 1999, *Breast Cancer Res. Treat.* 53:199-207). In addition to ADCC and ADCP, Fc regions of cell-bound antibodies can also activate the complement classical pathway to elicit complement-dependent cytotoxicity (CDC). C1q of the complement system binds to the Fc regions of antibodies when they are complexed with antigens. Binding of C1q to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see *Immunobiology*, $6^{th}$ ed., Janeway et al., Garland Science, N. Y., 2005, Chapter 2).

The term "antibody-dependent cellular cytotoxicity", or ADCC, is a mechanism for inducing cell death that depends upon the interaction of antibody-coated target cells with immune cells possessing lytic activity (also referred to as effector cells). Such effector cells include natural killer cells, monocytes/macrophages and neutrophils. The effector cells attach to an Fc effector domain(s) of Ig bound to target cells via their antigen-combining sites. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an Fc effector domain(s) of Ig.

The term "complement-dependent cytotoxicity", or CDC, refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A "cytotoxic effect" refers to the depletion, elimination and/or the killing of a target cell. A "cytotoxic agent" refers to an agent that has a cytotoxic effect on a cell. Cytotoxic agents can be conjugated to an antibody or administered in combination with an antibody.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an antibody or ADC is combined.

The phrase "pharmaceutically acceptable salt," refers to pharmaceutically acceptable organic or inorganic salts of an antibody or conjugate thereof or agent administered with an antibody. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

CHO cells refer to Chinese hamster ovary cells and include various strains including, for example, DG44, Dxb11, CHO-K, CHO-K1 and CHO-S.

The phrase "drug load" or "conjugation ratio" refers to the average number of drugs per antibody in an ADC solution or composition or reaction mixture.

Unless otherwise apparent from the context, the term "about" encompasses values within a standard deviation of a stated value.

DETAILED DESCRIPTION

I. General

The invention is based in part on the observation that a CHO cell oxidizing enzyme, particularly quiescin Q6 sulfhydryl oxidase 1 (QSOX1), can survive a seemingly rigorous antibody purification process and be present in a sufficient amount in an antibody preparation to lower subsequent conjugation loading efficiency of the antibody to a drug. Although the purification process may appear to result in an antibody having an acceptably low proportion of background contaminants/impurities to antibody, sufficient amounts of the oxidizing enzyme may nevertheless be present to result in sulfhydryl groups on the antibody being oxidized following antibody reduction and thus unavailable for conjugation to a drug. Although practice of the invention is not dependent on understanding of mechanism, persistence of QSOX1 through to the purified antibody product may be the result of interaction between the antibody and QSOX1 under some purification conditions. Whether the oxidizing enzyme survives the purification procedure depends on which purification techniques are employed, which can vary from one antibody to another. Before identification of the potential for the presence of a seemingly pure preparation of antibody with small but significant amounts of CHO cell oxidizing enzyme, a poor conjugation loading efficiency (reflected by inadequate mean ratio of drugs to antibody) may have been incorrectly attributed to any of numerous causes. However, with knowledge that contamination with a CHO cell oxidizing enzyme is a potential problem for subsequent conjugation, a suitable purification scheme can be devised for any antibody that eliminates or at least reduces CHO oxidizing enzyme(s) to an acceptable level.

II. CHO Cell Oxidative Enzymes

QSOX1 is the Chinese hamster homolog of human QSOX1, Swiss-Prot O00391. The enzyme catalyzes the oxidation of sulfhydryl groups to disulfides with the reduction of oxygen. Reference to QSOX1 refers to a full-length QSOX1 enzyme (with or without the signal peptide) and any fragment thereof, including naturally-occurring variants thereof, retaining sulfhydryl oxidizing ability whether naturally released by CHO cells or released as a result of an antibody purification process. QSOX1 in CHO cell culture media gives a band of apparent size range 65-75 kDa, or more specifically, 68-72 kDa. Exemplary QSOX1 fragments can comprise an extracellular domain, a thioredoxin domain and/or an ERV/ALR sulfhydryl oxidase domain. A predicted QSOX1 isoform X1 protein sequence has previously been identified as that set forth in SEQ ID NO:1 and found as GenBank Accession Number XP_003500174.1. The QSOX1 predicted isoform X1 protein sequence has since been updated. The updated sequence is as set forth in SEQ ID NO:2 and can be found as GenBank Accession Number XP_007639037.1. In some aspects, QSOX1 refers to a CHO cell oxidizing enzyme having 90% or higher (91%, 92%, 93%, 94%, 95%, 96%, 97%, 98% or 99% or 100%) sequence identity to SEQ ID NO:2 and retaining sulfhydryl oxidizing ability. In some aspects, QSOX1 refers to a CHO cell oxidizing enzyme comprising the amino acid sequence ranging from the 94$^{th}$ amino acid to the 571$^{rst}$ amino acid of SEQ ID NO:2 and retaining sulfhydryl oxidizing ability.

Other CHO cell enzymes that may be present as impurities include QSOX2 (CHO homolog of human Swiss-Prot Q6ZRP7) and the ALR (Activator of Liver Regeneration) sulfhydryl oxidase. For brevity, the following description refers primarily to QSOX1 but should be understood as referring alternatively or additionally to QSOX2, ALR or other CHO cells oxidizing enzymes surviving purification.

III. Purification Methods to Remove QSOX1 and Other CHO Cell Oxidizing Enzymes The application provides several techniques available to identify and to remove QSOX1 and other CHO cell oxidizing enzymes, such as QSOX2 or ALR (see Examples for more details). One technique is to load a preparation of antibody on a Protein A column, and wash under moderate or high salt conditions (e.g., at least 150 mM NaCl, or 150-500 mM NaCl). QSOX1 elutes from the column whereas the antibody remains bound. Another technique is depth filtration using e.g., a Millipore X0HC membrane. The antibody passes through the filter, whereas QSOX1 is trapped by the filter. Another technique is anion exchange chromatography, preferably using a strong anion exchanger with quaternary ammonium groups. A Capto-Q column from GE Healthcare is suitable. Under appropriate conditions (e.g., pH about 8 and conductivity about 5-7 mS/cm) the antibody flows though the column, whereas QSOX1 remains bound. A further technique is phenyl-membrane filtration. This type of membrane separates based on hydrophobic interactions. Under appropriate conditions (e.g., pH 6-8 and sodium citrate 0.35-0.4M), the antibody passes through and QSOX1 binds to the membrane.

IV. Testing for Removal

QSOX1 can be detected by a variety of assays, as further described in the Examples, including Western blot with an antibody specific to QSOX1. QSOX1 can also be detected by peptide sequence analysis or LC-MS/MS on a band of appropriate molecular weight (ca. 65-70 kDa depending on glycosylation state) excised from a gel. QSOX1 can also be detected by a functional assay. QSOX1 activity generates hydrogen peroxide, which can in turn be detected by a simple color change resulting from oxidation of Fe2+ in the presence of xylenol orange. The characteristic functional activity of QSOX1 is specifically inhibited by Zn2+ (e.g., at least 90%) but not EDTA and many other salts (KI, MnSO4, NaCl) or urea. QSOX1 can also be detected by a DTNB assay as demonstrated in Example 2.

QSOX1 is considered present if detectable above negative control levels (beyond experimental error) in any of the assays described below or in the examples. In some aspects, levels of QSOX1 as low as 1 ug/ml or 66 ppm can inhibit antibody drug loading efficiency. Thus, in some aspects, an acceptable level can mean less than 0.5 ug/ml or 33 ppm, and preferably less than 0.1 ug/ml or 6 ppm, or less than 0.01 ug/ml or 0.6 ppm. Preferably, the level of QSOX1 is within negative control levels as determined by any of the assays formats described in the Examples.

Alternatively or additionally, an acceptable level of QSOX1 can be defined as a level at or below which an acceptable conjugation ratio of drug to antibody can be obtained. An acceptable conjugation ratio is preferably one that is within 90%, 91%, 92%, 93%, 94%, 95%, 96%, 97%, 98%, or 99% of the target conjugation ratio. Parameters that can affect conjugation ratio and can be controlled to achieve a target conjugation ratio include, for example, the reductive conditions for the antibody (e.g. reductant type and concentration relative to antibody concentration), the concentration of drug-linker relative to antibody, the conjugation reaction time, and the conjugation reaction temperature. Preferably, the level of QSOX1 is such that it (a) does not prevent the correct extent of reduction from being achieved during the antibody reduction reaction and/or (b) it does not re-oxidize the reduced thiols immediately following reduction but prior to conjugation. In other words, preferably, the level of QSOX1 is such that it does not interfere with the reduction of the antibody or the stability of the reduced antibody.

Alternatively or additionally, an acceptable level of QSOX1 can be defined as a level that produces a value of 0.1 or less absorbance units in a DTNB assay or a ferrous oxidation xylenol orange assay. Briefly, a DTNB assay is one in which the reaction between free thiol groups in a control sample and test sample is measured and compared. See, for example, Example 2. In a ferrous oxidation xylenol orange assay, hydrogen peroxide is measured as an indicator of activity. See, for example, Example 1.

V. Work Flow Scheme

CHO cells are transformed with vector(s) encoding the chains of an antibody to be expressed and are cultured to express the antibody. Expression is usually initially conducted on a relatively small culture volume (e.g., 1-50 L) for purposes of providing sufficient antibody to determine a purification scheme. The culture media containing expressed antibody is then subject to at least one step of an antibody purification scheme to obtain a level of purity suitable for chemical conjugation or pharmaceutical use (e.g., at least 90, 95, 97, 98 or 99% w/w antibody to macromolecular contaminants/impurities). The purification scheme usually includes at least two column chromatography steps, at least one and usually multiple filtration steps, a viral inactivation step, and a concentration and resuspension/dilution step. After completion of any one or all of the purification steps, the antibody preparation can be tested for presence of QSOX1. If QSOX is detected above background of a negative control assay (beyond experimental error) or is detected above a level deemed unacceptable for subsequent conjugation, purification of the initial culture (or another similar culture if insufficient amount of the initial culture is available) is repeated with a second (different) purification step and/or scheme. The second purification step and/or scheme may differ from the first in the type of purification (e.g., anion vs. cation ion exchange chromatography, type of membrane used for filtration), or the buffers used for loading or elution, among other variations.

After or during conducting the second purification step/scheme, the resulting antibody preparation can be tested for QSOX1. If QSOX1 is detected at above background or above a level otherwise determined as acceptable, then purification is performed with a further purification scheme with or without further testing for QSOX1 enzyme. Whether after the first purification scheme, second or subsequent, a preparation of antibody is eventually obtained in which QSOX1 is either not detected above background or is detected but at a level deemed acceptable.

Having determined a purification scheme that reduces QSOX1 beyond the detection limit or at least to an acceptable level, a second culture, sometimes referred to as a production culture, of CHO cells is performed. Culture medium is subject to the purification step/scheme already determined to have been effective for purifying antibody and removing QSOX1. The resulting purified antibody is reduced and subsequently conjugated to an agent, e.g., a drug.

The second or production culture is typically larger than the primary culture used for determining a purification scheme. For example, the production culture may be at least 100 or 1000 times larger by volume than the primary culture. The production culture is typically performed repeatedly (batch culture) or continuously over a period of at least a year (e.g., over a period of at least five years), as is the purification of the antibody from that culture by the purification scheme previously determined to successfully purify the antibody without QSOX1.

In an alternative work flow, culture medium from CHO cells is subject to an antibody purification procedure without necessarily testing for QSOX1 enzyme, and the purified preparation is subject to chemical conjugation to a drug. If the conjugation loading efficiency (mean drug/antibody) is unexpectedly low (i.e., number of drug molecules to antibody is less than the target), then the purified preparation is tested for presence of QSOX1. If the enzyme is present at above background level or above a level deemed acceptable, then antibody is purified from CHO cell culture medium by a different purification method followed by testing for QSOX1 enzyme. Purification by a different method followed by testing for QSOX1 is then, if necessary, performed iteratively until a purification method is found that both purifies the antibody from contaminants/impurities in general to give an acceptable purity, and removes QSOX1 to background level or a level otherwise deemed acceptable for conjugation. When such a purification method is found, it can be used to prepare antibody from a second culture of CHO cells. The purified antibody is then conjugated to a drug via one or more free sulfhydryl groups.

VI. Conjugation of Antibodies to Drugs

Antibodies can be conjugated to cytotoxic or cytostatic moieties (including pharmaceutically compatible salts thereof) to form an antibody drug conjugate (ADC). Antibodies can be conjugated to agents other than drugs, for example, stability agents (e.g., PEG moieties). Particularly suitable moieties for conjugation to antibodies are cytotoxic agents (e.g., chemodrugs), prodrug converting enzymes, radioactive isotopes or compounds, or toxins (these moieties being collectively referred to as drugs). For example, an antibody can be conjugated to a cytotoxic agent such as a chemodrug, or a toxin (e.g., a cytostatic or cytocidal agent such as, e.g., abrin, ricin A, pseudomonas exotoxin, or diphtheria toxin).

For the purposes of the present invention, drugs are conjugated to antibodies, via sulfhydryl groups on the antibody. The sulfhydryl groups can be sulfhydryl groups on cysteine side chains. The cysteine residues can be naturally present in an antibody (e.g., interchain disulfides) or introduced by other means, e.g., mutagenesis. Methods of conjugating drugs to sulfhydryl groups on antibodies are well-known in the art (see, e.g., U.S. Pat. Nos. 7,659,241, 7,498,298, and International Publication No. WO 2011/130613). Antibodies are reduced prior to conjugation in order to render sulfhydryl groups available for conjugation. Antibodies can be reduced using known conditions in the art. Reducing conditions are those that generally do not cause any substantial denaturation of the antibody and generally do not affect the antigen binding affinity of the antibody. In one aspect, the reducing agent used in the reduction step is TCEP (tris(2-carboxyethyl)phosphine) and the TCEP is added at an excess for 30 minutes at room temperature. For example, 250 uL of a 10 mM solution of TCEP at pH 7.4 will readily reduce the interchain disulfides of 1 to 100 ug of antibody in 30 minutes at room temperature. Other reducing agents and conditions, however, can be used. Examples of reaction conditions include temperatures from 5° C. to 37° C. over a pH range of 5 to 8. The present inventors have found that oxidation of sulfhydryls to disulfides by an oxidizing enzyme such as QSOX1 after reduction by a reducing agent can render sulfhydryl groups unavailable for conjugation.

The drug can be conjugated to the antibody in a manner that reduces its activity unless it is cleaved off the antibody (e.g., by hydrolysis, by antibody degradation or by a cleaving agent). Such a drug is attached to the antibody with a cleavable linker that is sensitive to cleavage in the intracellular environment of a target cell but is not substantially sensitive to the extracellular environment, such that the drug is cleaved from the antibody when the ADC is internalized by the target cell (e.g., in the endosomal or, for example by virtue of pH sensitivity or protease sensitivity, in the lysosomal environment or in the caveolear environment).

Typically the ADC comprises a linker between the drug and the antibody. As noted supra, the linker may be cleavable under intracellular conditions, such that cleavage of the linker releases the drug from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Typically, the peptidyl linker is at least two amino acids long or at least three amino acids long. Cleaving agents can include cathepsins B and D and plasmin (see, e.g., Dubowchik and Walker, 1999, *Pharm. Therapeutics* 83:67-123). Most typical are peptidyl linkers that are cleavable by enzymes that are present in target cells. For example, a peptidyl linker that is cleavable by the thiol-dependent protease cathepsin-B, which is highly expressed in cancerous tissue, can be used (e.g., a linker comprising a Phe-Leu or a Gly-Phe-Leu-Gly (SEQ ID NO:3) peptide). Other such linkers are described, e.g., in U.S. Pat. No. 6,214,345. An exemplary peptidyl linker cleavable by an intracellular protease comprises a Val-Cit linker or a Phe-Lys dipeptide (see, e.g., U.S. Pat. No. 6,214,345, which describes the synthesis of doxorubicin with the Val-Cit linker). One advantage of using intracellular proteolytic release of the drug is that the agent is typically attenuated when conjugated and the serum stabilities of the conjugates are typically high.

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome.

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.).

The linker can also be a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

The linker also can be a non-cleavable linker, such as an maleimido-alkylene- or maleimide-aryl linker that is directly attached to the drug (e.g., a drug) and released by degradation of the antibody.

The linker is one that that comprises a functional group that is reactive to a group present on the antibody. In some aspects, the linker is linked to the antibody via a disulfide bond between a sulfur atom of the linker and a sulfur atom of the antibody. In other aspects, the linker forms a bond with a sulfur atom of the antibody via a maleimide group of the linker. In some aspects, the sulfur atom is from a cysteine residue of an interchain disulfide or from a cysteine residue introduced into the antibody (e.g., at position 239 according to the EU index).

Useful classes of cytotoxic agents to conjugate to antibodies include, for example, antitubulin agents, DNA minor groove binding agents, DNA replication inhibitors, chemotherapy sensitizers, pyrrolobenzodiazepine dimers or the like. Other exemplary classes of cytotoxic agents include anthracyclines, auristatins, camptothecins, duocarmycins, etoposides, maytansinoids and vinca alkaloids. Some exemplary cytotoxic agents include auristatins (e.g., auristatin E, AFP, MMAF, MMAE), DNA minor groove binders (e.g., enediynes and lexitropsins), duocarmycins, taxanes (e.g., paclitaxel and docetaxel), maytansinoids, benzodiazepines (e.g., pyrrolo[1,4]benzodiazepines, indolinobenzodiazepines, and oxazolidinobenzodiazepines), vinca alkaloids, doxorubicin, morpholino-doxorubicin, and cyanomorpholino-doxorubicin.

The cytotoxic agent can be a chemotherapeutic such as, for example, doxorubicin, paclitaxel, melphalan, vinca alkaloids, methotrexate, mitomycin C or etoposide. The agent can also be a CC-1065 analogue, calicheamicin, maytansine, an analog of dolastatin 10, rhizoxin, or palytoxin.

The cytotoxic agent can also be an auristatin. The auristatin can be an auristatin E derivative is, e.g., an ester formed between auristatin E and a keto acid. For example, auristatin E can be reacted with paraacetyl benzoic acid or benzoyl-valeric acid to produce AEB and AEVB, respectively. Other auristatins include AFP, MMAF, and MMAE. The synthesis and structure of various auristatins are described in, for example, US 2005-0238649 and US2006-0074008.

The cytotoxic agent can be a DNA minor groove binding agent. (See, e.g., U.S. Pat. No. 6,130,237.) For example, the minor groove binding agent can be a CBI compound or an enediyne (e.g., calicheamicin).

The cytotoxic or cytostatic agent can be an anti-tubulin agent. Examples of anti-tubulin agents include taxanes (e.g., Taxol® (paclitaxel), Taxotere® (docetaxel)), T67 (Tularik), vinca alkyloids (e.g., vincristine, vinblastine, vindesine, and vinorelbine), and auristatins (e.g., auristatin E, AFP, MMAF, MMAE, AEB, AEVB). Other suitable antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

The cytotoxic agent can be a maytansinoid, another group of anti-tubulin agents. For example, the maytansinoid can be maytansine or a maytansine containing drug linker such as DM-1 or DM-4 (ImmunoGen, Inc.; see also Chari et al., 1992, *Cancer Res.* 52:127-131).

Exemplary antibody drug conjugates include vcMMAE and mcMMAF antibody drug conjugates as follows wherein p represents the drug loading and ranges from 1 to 20 and Ab is an antibody:

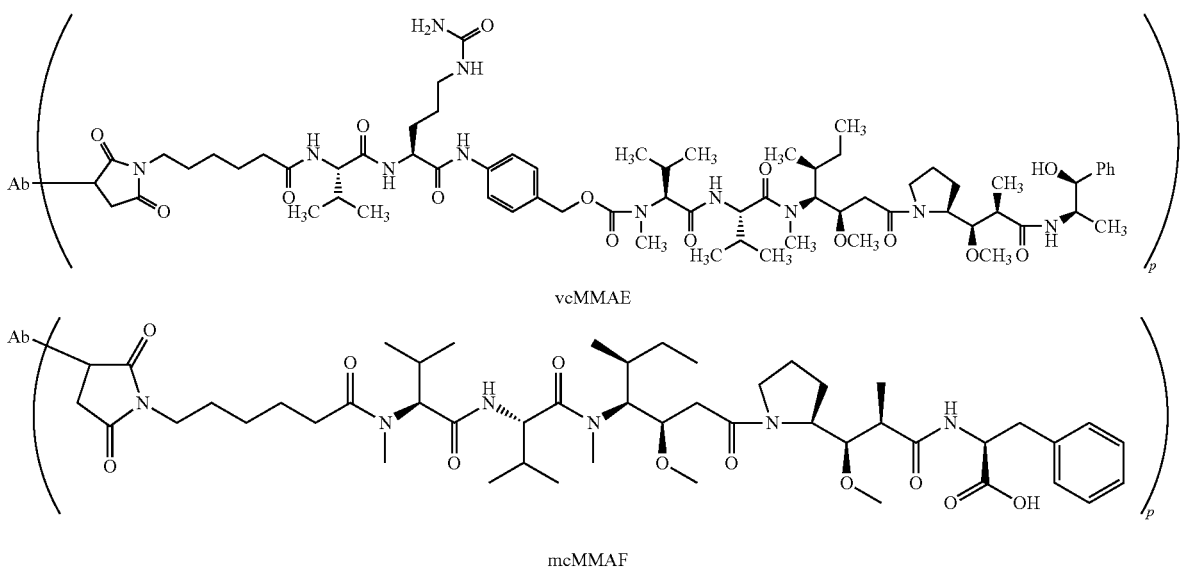

vcMMAE mcMMAF or a pharmaceutically acceptable salt thereof.

VII. Antibody Purification Methods

A large repertoire of techniques are known for purification of protein from CHO supernatant. These techniques include centrifugation, filtration, precipitation, viral inactivation and numerous types of column chromatography including protein-A, protein-G, protein-L, anion-exchange, cation exchange, mixed-mode, hydroxyapatite, size exclusion chromatography, and target affinity chromatography. Chromatography steps usually employ at least two buffers, one for loading and one for elution. Buffers can vary in pH and ionic strength, among other factors. An exemplary antibody purification includes at least one filtration step, at least one viral inactivation step, a protein-A column and at least one other column. Given the number of different techniques and possibilities for buffers, pH and other excipients in loading and elution solutions, the number of different purification procedures is very large. Suitable purification procedures for different antibodies are therefore often determined empirically to identify a procedure that both purifies the antibody to a level acceptable for pharmaceutical use (determined by ratio of antibody to macromolecular contaminants/impurities in general) and in which QSOX1 and/or other CHO cell oxidizing enzymes are reduced below a detectable level or at least to an acceptable level.

Ammonium sulfate precipitation can be used to enrich and concentrate antibodies from serum, ascites fluid or cell culture supernatant. As the concentration of this lyotropic salt is increased in a sample, proteins and other macromolecules become progressively less soluble until they precipitate. Antibodies precipitate at lower concentrations of ammonium sulfate than most other proteins and components of serum. The selectivity, yield, purity and reproducibility of precipitation depends on several factors, including time, temperature, pH and salt content.

Cellular contaminants of antibodies can be flocculated using acidic or cationic polyelectrolytes. Polyelectrolytes normally work by adsorbing to a particle to create an oppositely charged patch on the surface. This patch can then adhere to a bare patch on an opposing particle surface due to electrostatic attraction.

Depth filters can be used in the clarification of cell culture broths, to maintain capacity on membrane filters or to protect chromatography columns or virus filters. Depth filters are typically made of cellulose, a porous filter-aid such as diatomaceous earth and an ionic charged resin binder. Depth filters can employ both size exclusion and adsorptive binding to effect separation.

Membrane chromatography or membrane adsorbers function similarly to packed chromatography columns, but in the format of conventional filtration modules. Membrane chromatography uses microporous membranes, usually in multiple layers that contain functional ligands attached to the internal pore surface throughout the membrane structure. Commercially available Q membranes include ChromaSorb™ (Millipore), Mustang® (Pall) and Sartobind® (Sartorius). Around neutral to slightly basic pH and at low conductivities, viruses, DNA, endotoxin, a large population of host cell proteins and leached Protein A bind to the Q membrane, whereas the typically basic antibody molecules flow through the membrane matrix without being bound.

Ultrafiltration is a pressure-driven membrane process that is widely used for antibody concentration and buffer exchange. Ultrafiltration is a size-based separation in which species larger than the membrane pores are retained and smaller species pass through freely. Separation in ultrafiltration is achieved through differences in the filtration rates of different components across the membrane under a given pressure driving force. Buffer exchange is achieved using a diafiltration mode in which buffer of the final desired composition is added to the retentate system at the same rate in which filtrate is removed, thus maintaining a constant retentate volume. Ultrafiltration with membrane pores ranging from 1 to 20 nm can provide separation of species ranging in molecular weight from 500 daltons to 1,000 kilodaltons.

High performance tangential flow filtration (HPTFF) is a two-dimensional unit operation in which both size and charge differences are utilized for the purpose of purification and separation. Protein concentration and buffer exchange can be accomplished in the same unit operation.

Viruses can be inactivated by treatment at low pH and/or removed by various methods including filtration. Current virus-retentive filters are ultrafilters or microfilters with very small pores. Virus filtration membranes are made from hydrophilic polyethersulfone (PES), hydrophilic polyvinylidene difluoride (PVDF) and regenerated cellulose.

Ion exchange chromatography uses positively or negatively charged resins to bind proteins based on their net charges in a given buffer system Conditions (e.g., pH and ionic strength) can be determined that bind and release the target antibody with a high degree of specificity. Conversely, conditions can be found that bind nearly all other sample components except antibodies. Anion exchange chromatography uses a positively charged group, which can be weakly basic, such as diethylamino ethyl (DEAE) or dimethylamino ethyl (DMAE), or strongly basic, such as trimethylammonium ethyl (TMAE) or quaternary aminoethyl (QAE).

Cation exchange chromatography uses a resin modified with negatively charged functional groups. Cation and anion chromatograph are complementary techniques: molecules that bind strongly to one bind weakly if at all to the other.

Cation exchange columns can be strong acidic ligands such as sulphopropyl, sulfoethyl and sulfoisobutyl groups or weak acidic ligand such as carboxyl group. Cation exchange chromatography has been applied for purification processes for many mAbs with pI values ranging from about neutral or at little below (e.g., about 6) to basic. Most humanized IgG1 and IgG2 subclasses are good candidates for cation exchange chromatography, in which the antibody is bound onto the resin during the loading step and eluted through either increasing conductivity or increasing pH in the elution buffer. Negatively charged process-related impurities such as DNA, some host cell protein, leached Protein A and endotoxin are removed in the load and wash fraction. Cation exchange chromatography can also separate deamidated products, oxidized species and N-terminal truncated forms, as well as high molecular weight species from the desired antibody. Binding of antibodies on cation exchange resins depends on pH and conductivity, and resin type. SP Sepharose FF and SP Sepharose XL are two common commercially available resins.

Hydrophobic interaction chromatography (HIC) is a useful tool for separating proteins based on their hydrophobicity, and is complementary to other techniques that separate proteins based on charge, size or affinity. The sample is typically loaded on the HIC column in a high salt buffer. The salt in the buffer interacts with water molecules to reduce solvation of the protein molecules in solution, thereby exposing hydrophobic regions in the sample protein molecules that consequently bind to the HIC resin. The more hydrophobic the molecule, the less salt is needed to promote binding.

Immobilized metal chelate chromatography uses chelate-immobilized divalent metal ions (e.g., copper, cobalt or nickel) to bind proteins or peptides that contain clusters of three or more consecutive histidine residues. The strategy is most often used to purify recombinant proteins that have been engineered to contain a terminal 6×His fusion tag. IgGs are one of the few abundant proteins in serum (or monoclonal hybridoma cell culture supernatant) that possess histidine clusters capable of being bound by immobilized nickel. Conditions for binding and elution can be optimized for particular samples to provide gentle and reliable antibody purification.

Protein A, Protein G and Protein L, including recombinant versions thereof, are exemplary proteins used routinely for affinity purification of key antibody types from a variety of species. Protein A chromatography typically involves passage of clarified cell culture supernatant over the column at pH 6-8, under which conditions the antibodies bind and unwanted components such as host cell proteins and cell culture media components and viruses flow through the column. An optional intermediate wash step may be carried out to remove non-specifically bound impurities from the column, followed by elution of the product at pH 2.5-4. There are currently three major types of Protein A resins, classified based on their resin backbone composition: glass or silica-based, e.g., Prosep vA, Prosep vA Ultra (Millipore); agarose-based, e.g., Protein A Sepharose Fast Flow, MabSelect (GE Healthcare); and organic polymer based, e.g., polystyrene-divinylbenzene Poros A and MabCapture (Applied Biosystems). Several elution buffer components such as acetic acid, citric acid, phosphoric acid, arginine HCl and glycine HCl can be used depending on the antibody. The selection of elution pH is also dependent on the binding affinity of the antibody to the resin, antibodies with a higher binding affinity, requiring a lower elution pH.

Ceramic hydroxyapatite $(Ca_5(PO_4)_3OH)_2$ is a form of calcium phosphate that can be used often with a sodium phosphate gradient elution for separating antibodies from dimers, aggregates and leached Protein A among other contaminants.

Techniques for removing QSOX1, in particular, are described herein and in the Examples section and can be used in addition to, or in combination with, any of the above methods.

VIII. Exemplary Antibodies

The purification methods and work flows described can be used for any antibody, including non-human, humanized, human, chimeric, veneered, nanobodies, dAbs, scFV's, Fabs, and the like. The present methods are most useful for antibodies to be conjugated to an agent for diagnostic or therapeutic use. For example, the method are useful for antibodies to be conjugated to a drug for therapeutic use. Some such antibodies are immunospecific for a cancer cell antigen, preferably one on the cell surface internalizable within a cell on antibody binding. Targets to which antibodies can be directed include receptors on cancer cells and their ligands or counter-receptors (e.g., CD3, CD19, CD20, CD22, CD30, CD33, CD34, CD40, CD44, CD52 CD70, CD79a, Her-2, VEGF or VEGFR, CTLA-4, LIV-1, and nectin-4).

The present methods are also useful for purifying antibodies to be used to make ADC's for the treatment or prophylaxis of an autoimmune disease.

The present methods are also useful for purifying antibodies that bind to a receptor or a receptor complex expressed on an activated lymphocyte.

The present methods are also useful for purifying antibodies specific for a viral or a microbial antigen.

Some examples of commercial antibodies and their targets suitable for application of the present methods include alemtuzumab, CD52, rituximab, CD20, trastuzumab Her/neu, nimotuzumab, cetuximab, EGFR, bevacizumab, VEGF, palivizumab, RSV, abciximab, GpIIb/IIIa, infliximab, adalimumab, certolizumab, golimumab TNF-alpha, baciliximab, daclizumab, IL-2, omalizumab, IgE, gemtuzumab, CD33, natalizumab, VLA-4, vedolizumab alpha4beta7, belimumab, BAFF, otelixizumab, teplizumab CD3, ofatumumab, ocrelizumab CD20, epratuzumab CD22, alemtuzumumab CD52, eculizumab C5, canakimumab IL-1beta, mepolizumab IL-5, reslizumab, tocilizumab IL-6R, ustekinumab, and briakinumab IL-12. Optionally, the antibody is not brentuximab.

IX. Methods of Treatment and Pharmaceutical Compositions

ADCs produced in accordance with the methods described above are administered in an effective regime meaning a dosage, route of administration and frequency of administration that delays the onset, reduces the severity, inhibits further deterioration, and/or ameliorates at least one sign or symptom of the disease it is intended to treat, such as cancer, autoimmune disease or infection including any of the indications discussed above. If a patient is already suffering from the disease, the regime can be referred to as a therapeutically effective regime. If the patient is at elevated risk of the disease relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Dosages for an ADC typically vary depending on the drug component of the ADC. Exemplary doses can include for example, from 1.0 µg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 or 200-1500 mg as a fixed dosage. In some methods, the patient is administered a dose of at least 1.5 mg/kg, at least 2 mg/kg or at least 3 mg/kg, administered once every three weeks or greater. The dosage depends on the frequency of administration, condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration can also be localized directly, such as into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the ADC in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks over a continuous course of treatment, although more or less frequent dosing is also possible. For subcutaneous administration, an exemplary dosing frequency is daily to monthly, although more or less frequent dosing is also possible.

The number of dosages administered depends on the nature of the disease (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic (240-360 mOsm/kg) and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, ADC's can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 1-100 mg/ml, such as 10 mg/ml.

Treatment with ADC's of the invention can be combined with chemotherapy, radiation, stem cell treatment, surgery, anti-virals, antibiotics, immune suppressants or stimulants, or other treatments effective against the disorder being treated. Useful classes of other agents that can be administered with ADC's for treatment of cancers or autoimmune disease include, for example, antibodies to other receptors expressed on cancerous cells, antitubulin agents (e.g., auristatins), DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

In some aspects, treatment with the ADC's can increase the median progression-free survival or overall survival time of patients with tumors, especially when relapsed or refractory, by at least 30% or 40% but preferably 50%, 60% to 70% or even 100% or longer, compared to the same treatment (e.g., chemotherapy) but without an ADC. In some aspects, treatment (e.g., standard chemotherapy) can increase the complete response rate, partial response rate, or objective response rate (complete+partial) of patients with tumors by at least 30% or 40% but preferably 50%, 60% to 70% or even 100% compared to the same treatment (e.g., chemotherapy) but without the ADC.

Typically, in a clinical trial (e.g., a phase II, phase II/III or phase III trial), the aforementioned increases in median progression-free survival and/or response rate of the patients treated with standard therapy plus the ADC, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

EXAMPLES

Example 1: Evidence that QSOX1 is Present in Antibody Preparations Purified from CHO Cell Cultures Lot DEVNKB-1, which resulted from purification of an antibody expressed in CHO cells, unexpectedly exhibited poor drug conjugation. In contrast, lot L22042/E exhibited the desirable level of drug conjugation. Because drug conjugation to the antibody is mediated by free sulfhydryl groups, the presence of an impurity having oxidizing activity was suspected in lot DEVNKB-1. FIG. 1 shows the impact of the oxidizing impurity on the efficacy of drug conjugation to the antibody. The antibody from lot DEVNKB-1 (diamond symbols) shows reduced drug load as the time of reduction increases over 50 minutes, whereas the antibody from lot L22042/E (square symbols) shows a consistent and expected level of drug loading over the course of reduction.

Because certain preparations of other antibodies produced in CHO cells have been observed to have an oxidizing activity similar to that of lot DEVNKB-1, the source of the oxidizing activity was a matter of interest. To determine the source of the oxidizing activity, lot DEVNKB-1 was analyzed for the presence of a sulfhydryl oxidase by gel electrophoresis and Western blotting, and liquid chromatography-tandem mass spectrometry (LC-MS/MS).

Gel Electrophoresis and Western Blotting

Figure 2A:
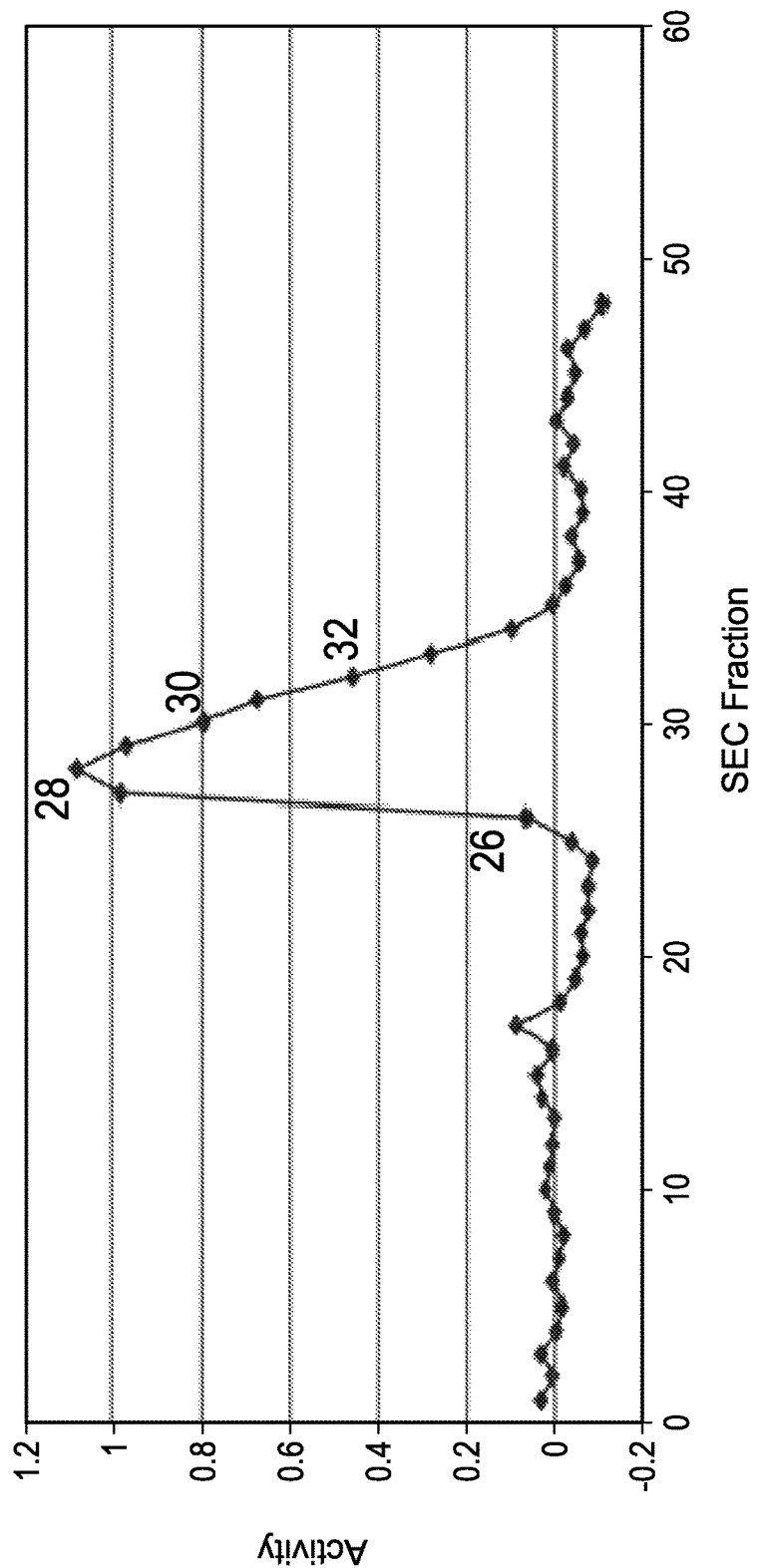
FIGS. 2a-2c: Oxidizing activity in an antibody preparation (lot DEVNKB-1) in fractions following SEC separation (FIG. 2a). Western blot of SEC fractions stained with anti-ALR (Activator of Liver Regeneration) and anti-QSOX1 antibodies (FIGS. 2b and 2c, respectively).
Figure 2B:
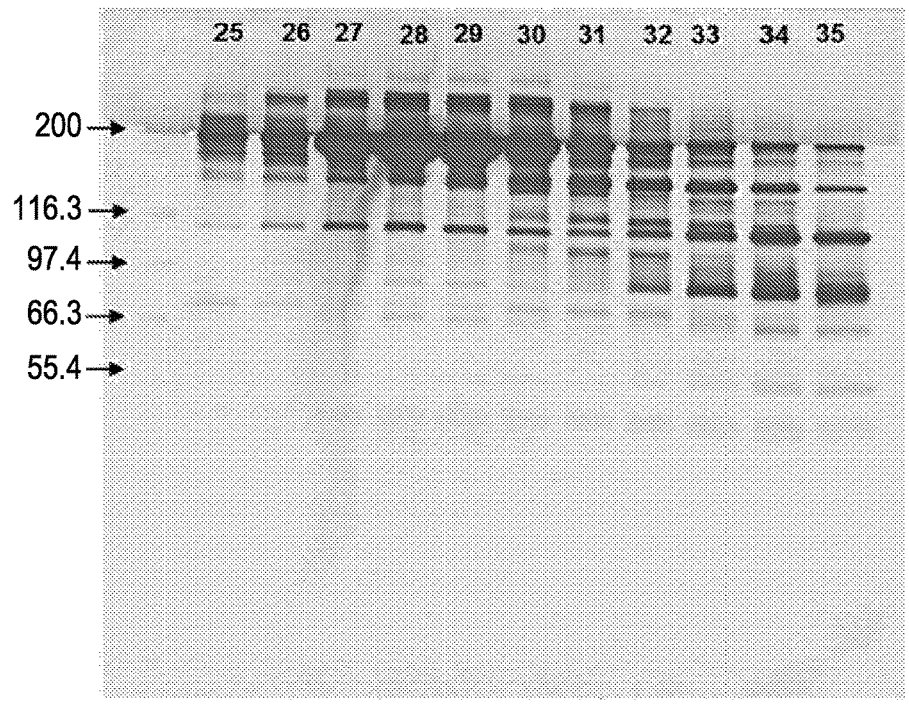
Figure 2C:
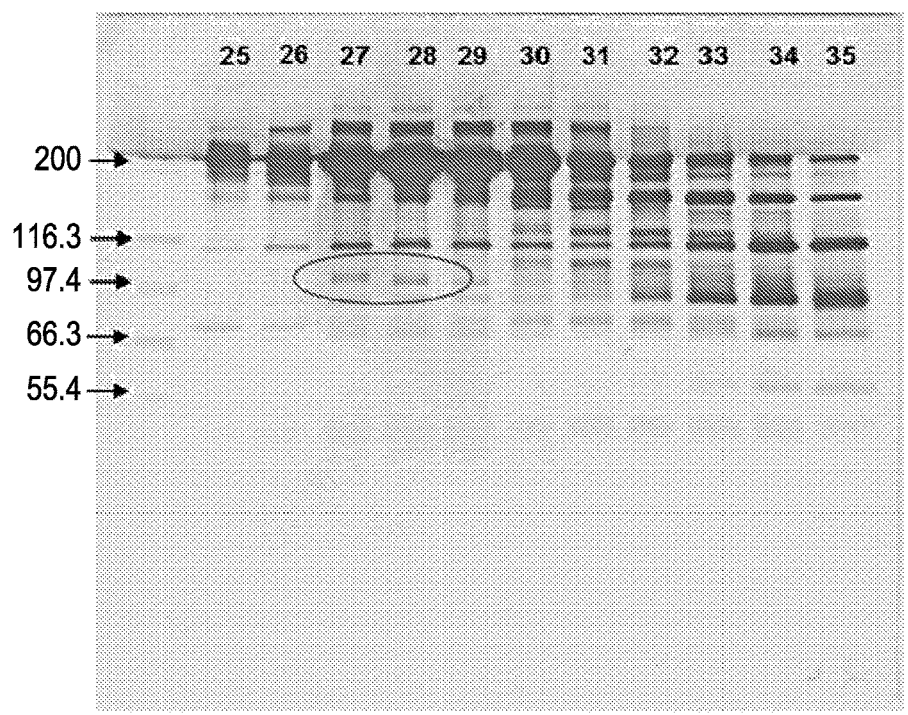

Comparison of lots DEVNKB-1 and L22042/E following separation by SDS-PAGE and silver staining did not reveal any protein bands obviously corresponding to the oxidizing activity (data not shown). To achieve better resolution, lot DEVNKB-1 was fractionated by size exclusion chromatography. Fractions were assayed for oxidizing activity as described in example 2. See FIG. 2a. Fractions corresponding to the peak activity were separated by SDS-PAGE, blotted, then stained with antibodies to candidate sulfhydryl oxidase proteins, including QSOX1, QSOX2, and ALR (Augmenter of Liver Regeneration). FIGS. 2b and 2c show the results of the Western blot analysis using anti-ALR and anti-QSOX1 primary antibodies, respectively, followed by a rabbit anti-goat IgG secondary antibody. The blots revealed extensive cross-reactivity between the secondary antibody and many product-related species. Nevertheless, a band in peak activity fractions 27-29 corresponding to a molecular weight between 65 kD and 70 kD was detected in the anti-QSOX1 blot (FIG. 2c), which is consistent with the predicted weight of hamster QSOX1 (70,356 Daltons).

LC-MS/MS Analysis

Figure 3A:
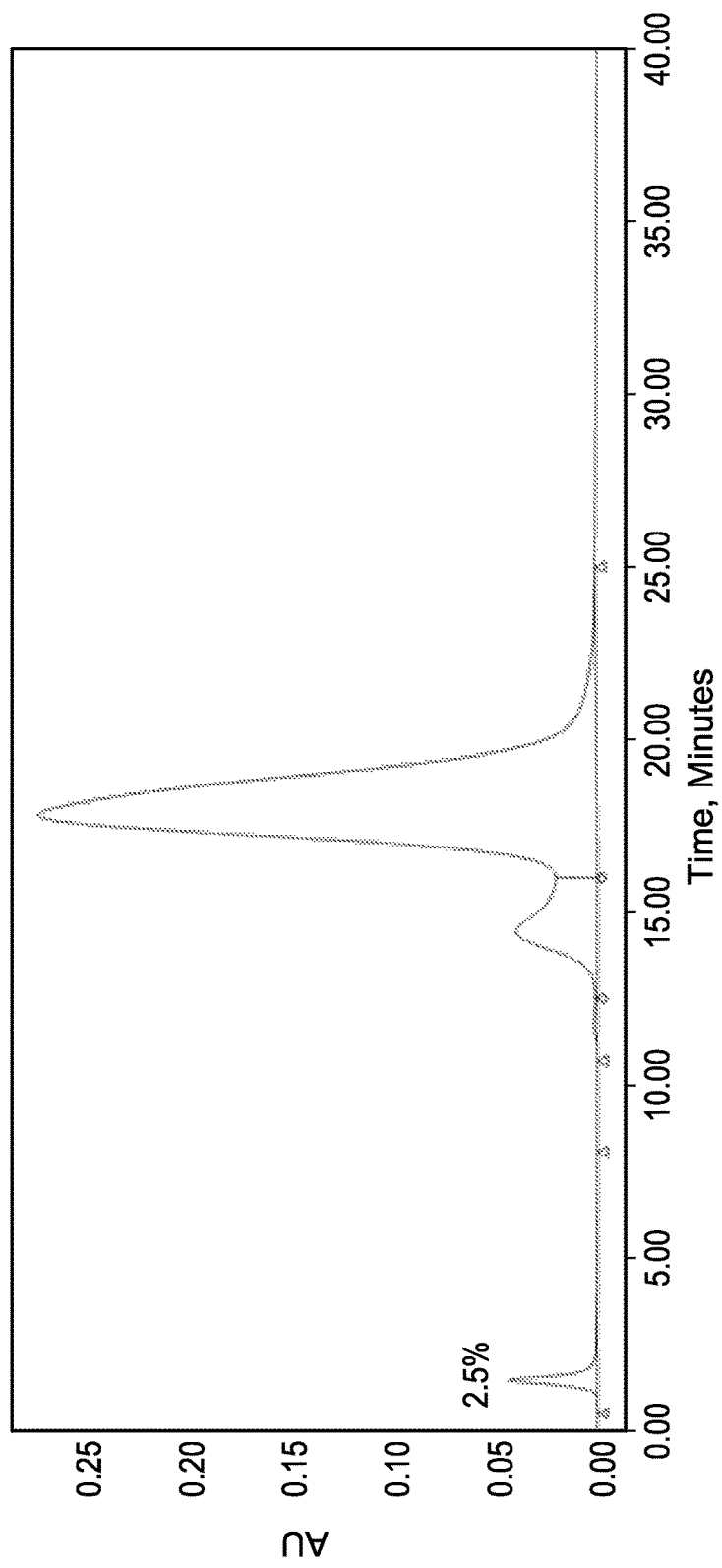
FIGS. 3a-c: Fractionation of an antibody preparation (lot DEVNKB-1) on a Poros Protein A column (FIG. 3a); oxidizing activity in each fraction (FIG. 3b); and image of SDS-PAGE gel showing protein contents of pooled fractions 3 and 4 (FIG. 3c). The arrow indicates a molecular weight consistent with 70 kDa QSOX1 and 76 kDa QSOX2.
Figure 3B:
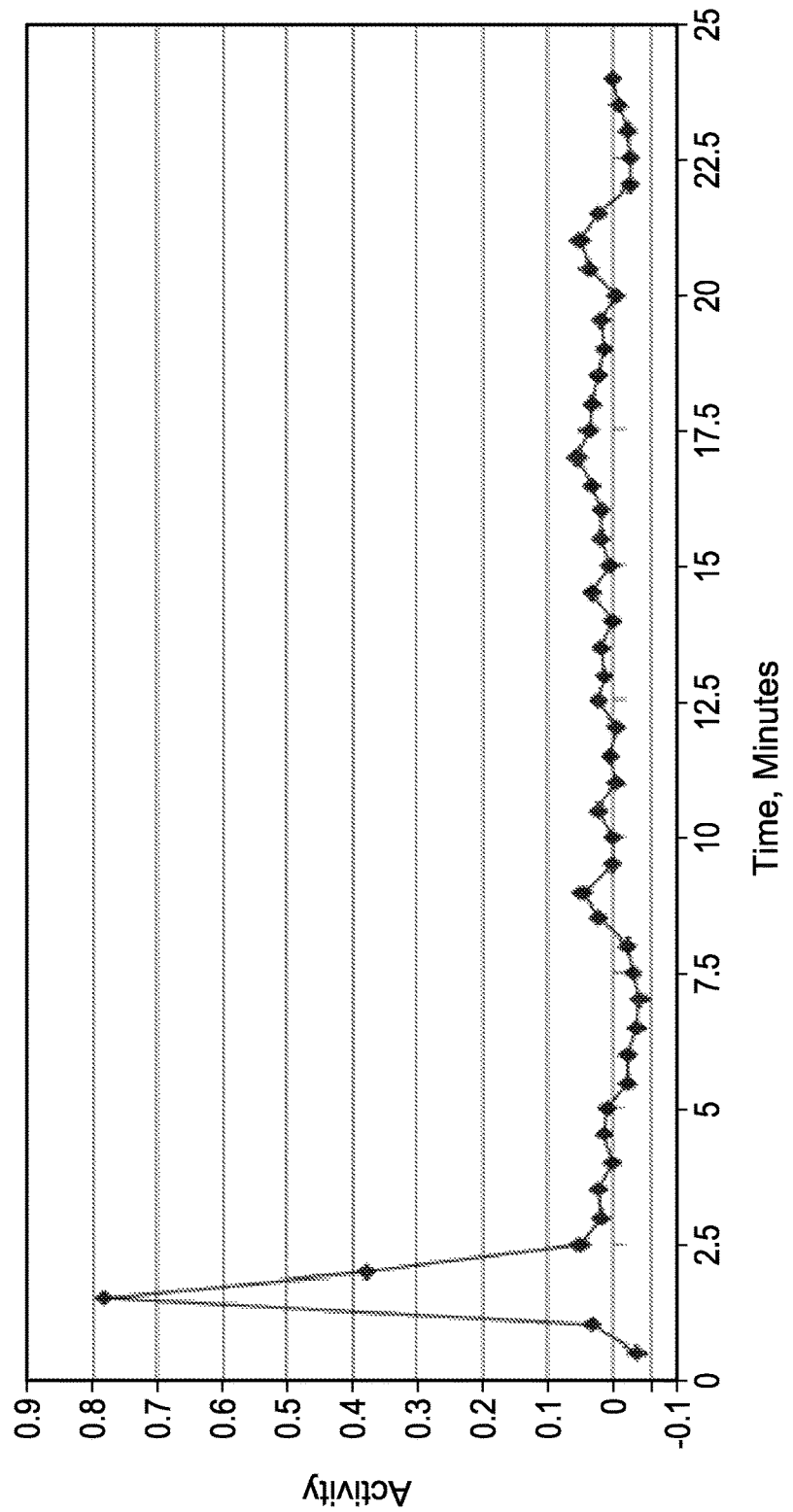
Figure 3C:
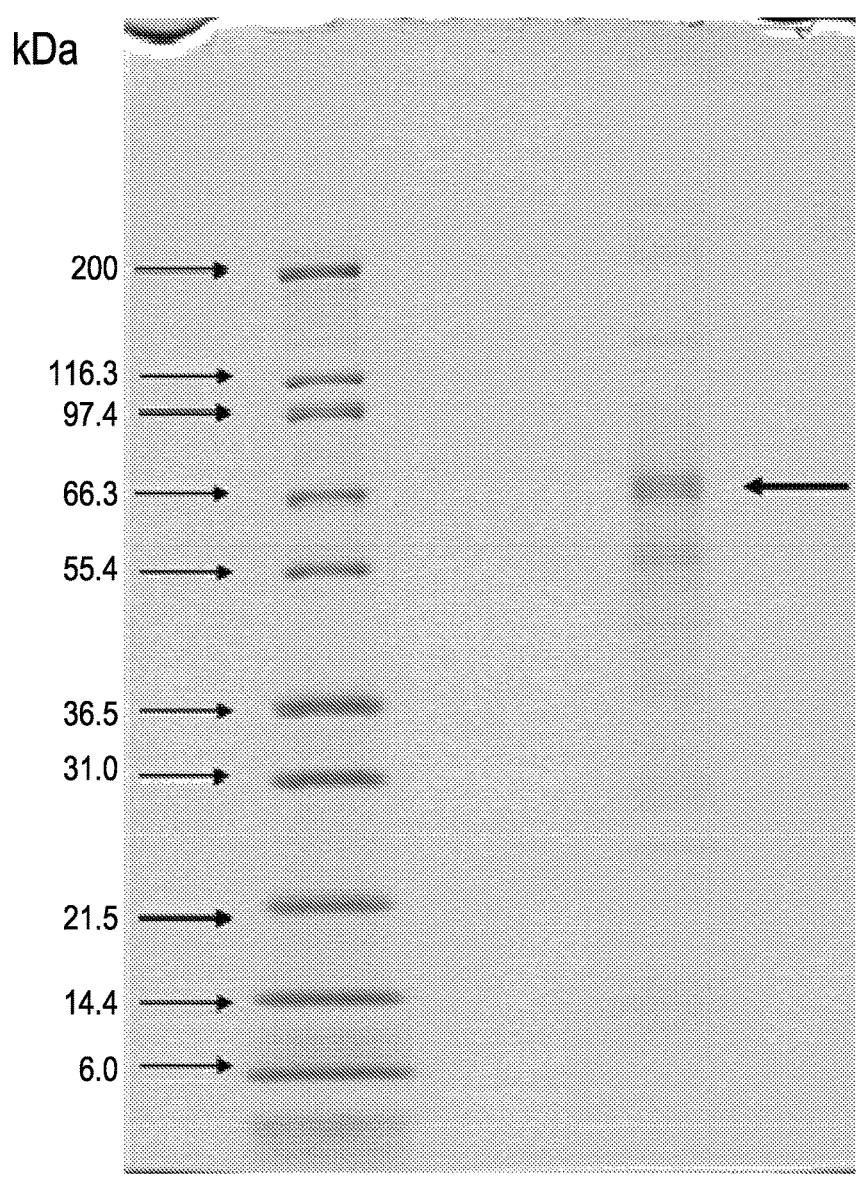

To identify the 65-70 kD protein detected in the anti-QSOX1 Western blot, lot DEVNKB-1 was fractionated by affinity chromatography on a Poros Protein A column. See FIG. 3a. Fractions were assayed for oxidizing activity as described in example 2. See FIG. 3b. Essentially all of the oxidizing activity came out in fractions 3 and 4. Fractions 3 and 4 from a series of three runs were pooled and analyzed by SDS-PAGE. See FIG. 3c. The most prominent band was in the 65-70 kD range and formed a diffuse single band or doublet, consistent with the Western blot. Using gel digestion and LC-MS/MS, the band was positively identified as QSOX1.

Oxidizer Characterization

Further to characterize the oxidizing activity in lot DEVNKB-1, the lot was tested for sulfhydryl oxidizing activity using the ferrous oxidation xylenol orange (FOX) assay. Sulfhydryl oxidases catalyze the following reaction:

$$2R-SH+O_2 \rightarrow R-S-S-R+H_2O_2$$

As the reaction proceeds, oxygen is consumed and hydrogen peroxide is produced. The hydrogen peroxide by-product can be detected readily and reliably, and thus serves as a proxy for sulfhydryl oxidase activity. In the FOX assay, hydrogen peroxide oxidizes ferrous iron ($Fe^{2+}$) to produce ferric iron ($Fe^{3+}$). The ferrous iron then complexes with xylenol orange to form a compound that absorbs 560 nm light. Thus, by monitoring absorption of 560 nm light (e.g., using a spectrophotometer), the amount of sulfhydryl oxidizing activity in a sample can be determined. The value of a negative control is compared to the value of the test sample by determining the difference in the 560 nm reading. If the resulting value is greater than 0.1 absorbance units, then the samples is positive for oxidizing impurity. As shown in Table 1, the presence of DEVNKB-1 resulted in a 560 nm absorption of 0.70-0.80. Addition of both DEVNKB-1 and 1 mM $Zn^{2+}$, however, was only 0.008. The data show that 1 mM $Zn^{2+}$ can essentially eliminate the oxidizing activity in lot DEVNKB-1. This is consistent with the oxidizing agent having a flavin-dependent sulfhydryl oxidase domain, such as QSOX1.

TABLE 1

| Additive | DEVNKB-1 + | DEVNKB-1 − | Difference | % Activity |
|---|---|---|---|---|
| — | 0.81047 | 1.53920 | 0.72873 | 100% |
| — | 0.80907 | 1.58360 | 0.77453 | |
| 1 mM Zn2+ | 1.48020 | 1.48810 | 0.00790 | 1% |

Further assays were performed to see whether EDTA could reverse the $Zn^{2+}$-dependent elimination of oxidizing activity in lot DEVNKB-1. In these experiments, $Zn^{2+}$ was added to the assay buffer, either with or without EDTA. In addition, assay buffer having EDTA was evaluated. As shown in Table 2, the oxidizing activity associated with lot DEVNKB-1 was reduced 95% by the presence of $Zn^{2+}$ relative to assay buffer that contained additional EDTA. Addition of both $Zn^{2+}$ and additional EDTA, however, reduced the oxidizing activity by only 6%. Thus, the EDTA effectively reversed the $Zn^{2+}$-dependent inhibition of oxidizing activity. Again, this is what is expected for an oxidizing agent that has a flavin-dependent sulfhydryl oxidase domain, such as QSOX1.

TABLE 2

| Additive | DEVNKB-1 + | DEVNKB-1 − | Difference | % Activity |
|---|---|---|---|---|
| 1 mM $Zn^{2+}$ | 1.50550 | 1.53647 | 0.03097 | 5% |
| 1 mM $Zn^{2+}$ + EDTA | 0.99833 | 1.53647 | 0.53814 | 94% |
| EDTA | 0.96444 | 1.53647 | 0.57203 | 100% |

Based on the Western blot data, the LC-MS/MS data (not shown), and the characterization of the oxidizing activity, the oxidizing activity in lot DEVNKB-1 was determined to be the QSOX1 sulfhydryl oxidase.

Example 2: Assays to Detect QSOX1 in CHO Cell Cultures

To provide for detection of oxidizing activity in antibody preparations (e.g., when the antibody is intended for conjugation to a drug), an assay was developed that uses partially reduced SGN-30 (cAC10 antibody, which is the antibody component of brentuximab vedotin as a substrate. SGN-30 was selected as the substrate because cAC10 antibody has been consistently purified without QSOX1 contamination. Other well-characterized substrates having free thiols can be used in place of SGN-30.

The assay involves incubating substrate (e.g., SGN-30) with a test sample for a fixed amount of time, then detecting the amount of free sulfhydryl groups in the substrate using DTNB (5,5'-dithiobis-(2-nitrobenzoic acid), also known as Ellmans' reagent).

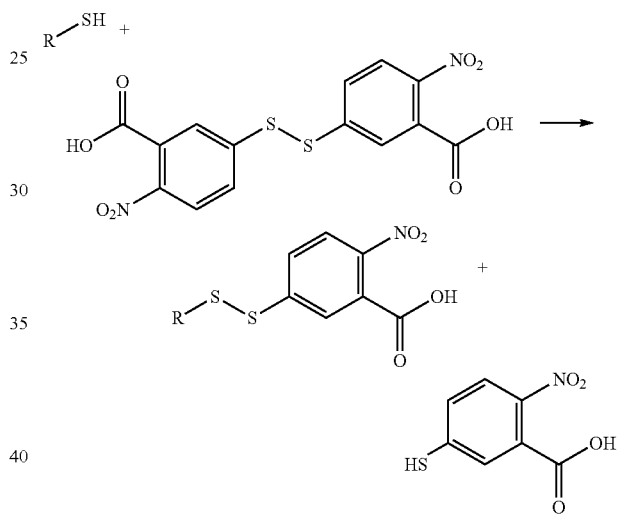

Free thiol groups in the substrate react with DTNB, cleaving the disulfide bond and producing 2-nitro-5-thiobenzoate ($NTB^-$), which ionizes to $NTB^{2-}$ in water at neutral and alkaline pH. $NTB^{2-}$ has a yellow color and can be rapidly quantified using a spectrophotometer and measuring the absorbance of visible light at 412 nm. If oxidizing impurities are present in the test sample, free sulfhydryl groups on the substrate (e.g., in cysteine residues not already involved in a disulfide bond) are oxidized into disulfide bonds, resulting in fewer free thiols. Thus, there is less reaction between substrate and DTNB, resulting in a lower production of yellow color and a correspondingly lower absorption of 412 nm light by the sample.

The reaction between DTNB and free thiol groups is rapid and stoichiometric. Accordingly, if desired, the amount of free sulfhydryl groups in the substrate can be quantified using a molar extinction coefficient of 14,150M-1 cm-1 (suitable for dilute buffer solutions).

Materials used in the assay include Spectrophotometer (e.g., Agilent model 8453); Quartz cuvette (e.g., Starna, 16.50-Q-10/Z15); 1 M Tris HCl, pH 7.4; 0.5M EDTA, pH 8.0; Potassium phosphate monobasic; Potassium phosphate dibasic; Polysorbate 80; DTNB (e.g., Sigma D218200).

The assay involves spectrophotometric analysis of at least a negative control sample, a positive control, a test sample, and a spectrophotometer blank. Additional control and/or test samples can be analyzed as needed. The composition of the control and test samples are as shown in Table 3. The buffer used in the assay is 10 mM Potassium phosphate, 0.2 mg/mL Polysorbate 80, pH 6.0. However, other dilute buffers are also suitable depending on the buffer of the test sample to be analyzed. The final volume of the samples to be assayed in 150 µL, but that can also be adjusted as needed. To simplify the assay, a mastermix cocktail containing the buffer, EDTA, water, and substrate (e.g., partially reduced cAC10) can be prepared, with the assay being initiated upon addition of 50 µL of sample to 100 µL of mastermix cocktail.

TABLE 3

|  | 1M Tris, pH 7.4 | 0.5M EDTA pH 8.0 | Water | Partially Reduced cAC10 | Sample |
|---|---|---|---|---|---|
| Negative Control | 15.0 µL | 3.0 µL | 7.0 µL | 75.0 µL | 50.0 µL Buffer |
| Positive Control | 15.0 µL | 3.0 µL | 7.0 µL | 75.0 µL | 50.0 µL REFNKB-1 |
| Test Sample | 15.0 µL | 3.0 µL | 7.0 µL | 75.0 µL | 50.0 µL Test Sample |
| Spectro. Blank | 75.0 µL | 15.0 µL | 35.0 µL | 625.0 µL Buffer | |

Sample preparation and analysis is performed as follows. Microfuge tubes are labeled corresponding to the samples and controls to be analyzed. 100 µL of mastermix cocktail is placed in each tube. 50 µL of each sample is added to the corresponding control/test sample tube. The tubes are mixed by vortexing. The tubes are placed in a 37° C. waterbath or incubator and incubated for 2 hrs. A second microfuge tube for each sample is labeled and 100 µL of 1 mM DTNB is placed in each tube. At the conclusion of the 2 hr. incubation, the samples are removed from the waterbath/incubator and 100 µL of sample is transferred to the corresponding microfuge tube containing 100 µL of DTNB. The tubes are mixed by vortexing. The samples are incubated at room temperature for at least 5 minutes, then absorbance is determined. Absorbance is measured at 412 nm and corrected for absorbance at 700 nm (i.e., determine $A_{412}$-$A_{700}$). Spectra can be collected from 200 to 700 nm.

To assess the presence of an oxidizing impurity in a test sample, the value (412 nm-700 nm) of the negative control (Buffer) is compared to the value of the test sample by determining the difference in the 412 nm reading. If the resulting value is greater than 0.1 absorbance units, then the sample is positive for oxidizing impurity.

When testing culture medium from an antibody culture, the assay typically produces high values (~0.5 AU), suggesting high levels of oxidizer. However, the assay readout is color based and the color in the cell culture media tends to interfere with the assay readout. Consequently, it is difficult to definitively measure oxidizing impurity in clarified harvest using this assay. Oxidizing impurity is preferably measured following at least one purification step, e.g., after at least one chromatography step (e.g., after protein A, ion exchange, or HIC chromatography).

This assay measures sulfhydryl oxidase activity generally, including activity arising from QSOX1, QSOX2, ALR, and other enzymes. More specific assays for specific sulfhydryl oxidases can also be used, e.g., as described in Example 1.

Example 3: Methods to Remove QSOX1

Reduction of Oxidizing Impurity by Implementation of a Salt Wash on Protein A

A preparation of a second antibody referred to herein as Antibody 2 was found to have unacceptably high levels of oxidizing activity (following clarification via centrifugation and filtration). To remove the oxidizing impurity, protein A chromatography with salt washes of varying strength was assessed.

A 3.2 cm diameter by 23.2 cm bed height (193.2 mL bed volume) MabSelect Sure Protein A column was equilibrated with 25 mM Tris, 50 mM NaCl, pH 7.5, and then loaded to 25 g of mAb/L of packed bed. After loading, the column was washed with 50 mM Tris buffered solutions containing various levels of NaCl, as shown in Table 4. Antibody elution was performed using 25 mM acetate pH 3.4. Flow rate was held constant at 4 minute residence time.

The level of oxidizing impurity in column eluates was analyzed using the assay of Example 2. The data (see Table 4) show that the oxidizing impurity was not contained in the Protein A eluate when washed with a moderate (150 mM NaCl) or high (500 mM NaCl) concentration of salt. A wash containing a low concentration of salt (50 mM NaCl) was ineffective at reducing the level of oxidizing impurity below the 0.1 absorbance threshold. The wash from the high concentration salt contained a high level of oxidizing impurity, demonstrating that the high concentration salt wash desorbed the impurity from the column resin or mAb.

The results generally indicate that the affinity of the oxidizing impurity for the protein A ligand, resin backbone, and/or mAb is disturbed by high ionic strength solutions, consistent with an ionic interaction.

TABLE 4

| Sample ID | Difference A412 | Presence of oxidizing impurity |
|---|---|---|
| Eluate (Low, 50 mM, Salt wash) | 0.407 | positive |
| Eluate Moderate, 150 mM, Salt wash | 0.095 | negative |
| Eluate High, 500 mM, Salt Wash | 0.053 | negative |
| High NaCl wash fraction | 0.910 | positive |
| DEVNKB_1 (Pos Control) | 0.573 | positive |
| Buffer_1 (Neg control) | −0.020 | negative |

Depth Filtration

Depth filtration was also tested for its ability to remove oxidizing impurity. The depth filter, a Millipore X0HC filter, was wetted with 50-100 L/m² of water and equilibrated with at least 15 L/m² of equilibration buffer (e.g., pH of 7.5-8 and the NaCl concentration from 50-100 mM). Filtration was performed at 230 L/m²/hr. (LMH) at targeted load factor of 20-60 L/m². To recover product the filter was flushed with equilibration buffer of sufficient volume to ensure that target peak collection was reached. The filtrate was collected by absorbance at 280 nm. Using such conditions, the oxidizing impurity was removed.

Anion Exchange—Capto Q

It was observed that a Capto Q strong anion exchange column (GE Healthcare Life Sciences, Catalog #17-5316) resulted in removal of oxidizing impurity when operated at flow-through mode with a buffer at a pH of 8.0 and a conductivity<8 mS/cm (e.g., 5-7 mS/cm). These conditions provide a starting point for assessing removal of oxidizing impurity using a Capto Q column. It was demonstrated for the antibody 1 that a buffer having low conductivity and high pH is required for effective clearance of oxidizing impurity. The Capto Q column was operated in flow-through mode. At appropriate conditions, the mAb was unretained by the resin, whereas the oxidizing impurity was adsorbed by the resin. The oxidizing impurity was later stripped from the resin using a high salt buffer. For a second antibody, antibody 2, as shown in Table 5, effective clearance was demonstrated at a pH of 7.5 (7.5-8 is effective), provided that the conductivity of the buffer was 11 mS/cm (conductivity of less or equal to 11 is required). Buffers having a pH of 7 and conductivity ranging from 11 to 15 mS/cm were ineffective at separating the impurity from the mAb in a flow-through mode, as was a buffer having a pH of 7.5 and conductivity of 15 mS/cm.

TABLE 5

| Sample ID | Difference, A412 nm | Presence of Oxidizing Impurity |
|---|---|---|
| pH 7/cond 11 | 0.200 | positive |
| pH 7/cond 15 | 0.227 | positive |
| pH 7.5/cond 11 | −0.006 | negative |
| pH 7.5/cond 15 | 0.190 | positive |
| Capto Q load | 0.415 | positive |
| Buffer control | −0.020 | negative |

Phenyl Membrane

Sartobind Phenyl®, when operated in flow-through mode, has also been found to effectively clear oxidizing impurity from antibody preparations produced in CHO cells. Under appropriate conditions, the oxidizing impurity is retained by the membrane while the mAb is not. The oxidizing impurity can be later stripped from the resin using a low salt buffer. The load is prepared by diluting the antibody to a target citrate molarity (typically 0.3-0.4 M sodium citrate) and pH (typically 6-8). The membrane is equilibrated in 5 membrane volumes (MV) of equilibration buffer selected to match the diluted antibody load. The diluted load is then applied to the membrane, and the membrane is washed with 10 MV of equilibration buffer. The antibody preparation, free of oxidizing impurity, comes out in the flow through. Bound material is eluted with, e.g., 50 mM Tris, pH 8, and the membrane is regenerated with, e.g., 5 MV of 25 mM sodium phosphate, 20% IPA at pH 6.5. The process is operated at 10 mL/min or 3.3 MV/min. The entire peak of the flow-though is collected, e.g., from 0.1-0.1 AU at 280 nm using a 2 mm flow path.

Table 6 provides data from a purification step on phenyl membrane. The level of oxidizing impurity measured in the phenyl flow-through ranged from 0.1 to 0.04 absorbance units.

TABLE 6

| Sample | Δ A412 | Oxidizer Impurity |
|---|---|---|
| Phenyl Membrane Load | 0.41 | Positive |
| Phenyl Membrane FT | −0.06 | Negative |

To determine the operational robustness for using a phenyl membrane, the oxidizing impurity present in Antibody 2, preparations was evaluated after applying the phenyl membrane purification step at different conditions of pH and citrate molarity. See Table 7. To reduce the level of oxidizing impurity in the flow-through, the molarity of citrate is preferably operated at the upper limit, 0.4M.

TABLE 7

| pH | Citrate Molarity | Oxidizing Impurity (Δ 412 nm) | Presence of Oxidizing Impurity |
|---|---|---|---|
| 6 | 0.35 | 0.05 | Negative |
| 8 | 0.40 | 0.00 | Negative |
| 6 | 0.40 | −0.04 | Negative |
| 7 | 0.40 | −0.03 | Negative |
| 7 | 0.30 | 0.10 | Positive |
| 8 | 0.35 | 0.02 | Negative |
| 8 | 0.30 | 0.09 | Negative |
| 6 | 0.30 | 0.12 | Positive |
| 7 | 0.35 | 0.04 | Negative |
| 7 | 0.35 | 0.03 | Negative |

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

```
Sequence listing:
```
SEQ ID NO: 1:
MATGLRRREYIWLLWALTITVSYLVALFSHLLRILTVKKLQWRPVLNLAV

LDCAEETNTAVCRDFNISGFPTVRFFKAFSKNGSGITLPVADASVETLRR

KLIDALESHSDMWSSSRPKLKPAKLVEINEFFAETNEDYLVLIFEDKDSY

VGREVTLDLFQHHIPVHRVLNTERNAVSKFGVVEFPSCYLLFRNGSFSRV

PVVMESRLFYTSYLKGMSGPILVDPPTTTISTDAPVTTDVVPTVWKVANH

ARIYMADLESSLHYIFLVEVGKFSVLEGQRLLALKKLVAVLAKYFPGRPL

AQNFLHSIHDWLQRQQRKKIPYKFFRAALDNRKEGIVLTEKVNWVGCQGS

Sequence listing:

KPHFRGFPCSLWILFHFLTVQASRYSENHPQEPADGQEVLQAMRSYVQWF

FGCRDCAEHFENMAASTMHRVRSPTSAVLWLWTSHNKVNARLSGAPSEDP

YFPKVQWPLRELCFDCHNEINGREPVWDLEATYRFLKAHFSSENIILDTP

VAGLATQRNPQILGATPEPVMDALELETRNSVLGHERAASTESPGATALN

VPVGKPEASGPQALYTGQGPPEHMEEPQRVTQGHTQGQQHLSKRDTEVLT

LPEVNHLQGPLELRRGGRSPKQLVNIPEGEPEAPAIRGQGPWLQVLGRGF

SHLDISLCVGLYSVSFVCLLAMYTYFRARLRTPKGHLVTQ

SEQ ID NO: 2:
MRRCGRHSGS PSQMLLLLLP PLLLAVPGAG AVQVSVLYSS

SDPVTVLNAN TVRSTVLRSN GAWAVEFFAS WCGHCIAFAP

TWKELAYDVR EWRPVLNLAV LDCAEETNTA VCRDFNISGF

PTVRFFKAFS KNGSGITLPV ADASVETLRR KLIDALESHS

DMWSSSRPKL KPAKLVEINE FFAETNEDYL VLIFEDKDSY

VGREVTLDLF QHHIPVHRVL NTERNAVSKF GVVEFPSCYL

LFRNGSFSRV PVVMESRLFY TSYLKGMSGP ILVDPPTTTI

STDAPVTTDV VPTVWKVANH ARIYMADLES SLHYIFLVEV

GKFSVLEGQR LLALKKLVAV LAKYFPGRPL AQNFLHSIHD

WLQRQQRKKI PYKFFRAALD NRKEGIVLTE KVNWVGCQGS

KPHFRGFPCS LWILFHFLTV QASRYSENHP QEPADGQEVL

QAMRSYVQWF FGCRDCAEHF ENMAASTMHR VRSPTSAVLW

LWTSHNKVNA RLSGAPSEDP YFPKVQWPLR ELCFDCHNEI

NGREPVWDLE ATYRFLKAHF SSENIILDTP VAGLATQRNP

QILGATPEPH M

SEQ ID NO: 2:
GFLG

---

What is claimed is:

1. A method of producing a conjugated antibody, comprising:
   (a) performing at least one purification step of a purification scheme to obtain at least a partially purified preparation of an antibody from a culture of CHO cells expressing the antibody;
   (b) testing the preparation for presence of a CHO cell sulfhydryl oxidizing enzyme;
   (c) if the enzyme is detected at a level greater than 0.5 µg/ml or 33 ppm in the preparation of step (b), repeating steps (a) and (b);
   (d) if the enzyme is detected at a level less than 0.5 µg/ml or 33 ppm in the preparation of step (b), performing the at least one purification step to obtain at least a partially purified preparation of antibody, wherein the at least one purification step of the purification scheme comprises at least one of a step of (i) washing a protein A column with a salt wash at a concentration of 150-500 mM NaCl, (ii) performing depth filtration at 230 L/m²/hr and using at least 15 L/m² of an equilibration buffer with a pH of 7.5-8 and NaCl concentration of 50-100 mM, (iii) using anion exchange with a quaternary ammonium ion column with a buffer having a pH of 7.5-8 and a conductivity of less than or equal to 11 mS/cm, and (iv) performing phenyl membrane filtration using a buffer having a pH of 6-8 and 0.3-0.4M sodium citrate; and
   (e) conjugating the at least partially purified antibody via one or more sulfhydryl groups to a cytotoxic drug to produce the conjugated antibody.

2. The method of claim 1, wherein the CHO cell sulfhydryl oxidizing enzyme is selected from at least one of quiescin Q6 sulfhydryl oxidase 1 (QSOX1), Q6 sulfhydryl oxidase 2 (QSOX2), and Augmenter of Liver Regeneration (ALR).

3. The method of claim 2, wherein the CHO cell sulfhydryl oxidizing enzyme is QSOX1.

4. The method of claim 1, wherein steps (d) and (e) are performed multiple times on different cultures of the antibody over a period of at least a year.

5. The method of claim 1, wherein the testing comprises identifying a band of 65-75 kDa on a gel.

6. The method of claim 5, wherein the band is identified by western blot or silver stain.

7. The method of claim 1, wherein the testing comprises a functional test for QSOX1 activity.

8. The method of claim 7, wherein the functional test produces hydrogen peroxide as an indicator of the activity.

9. The method of claim 8, wherein the activity is inhibited by zinc ions, which inhibition is reversed by EDTA.

10. The method of claim 1, wherein the antibody is not brentuximab.

11. The method of claim 1, wherein the cytotoxic drug is selected from anti-tubulin agents, DNA minor groove binding agents, DNA replication inhibitors, chemotherapy sensitizers and pyrrolobenzodiazepine dimer.

12. A method of producing a conjugated antibody, comprising:
purifying an antibody from a culture of CHO cells by anion exchange with a quaternary ammonium ion column using a buffer having a pH of 7.5-8 and a conductivity less than or equal to 11 mS/cm, wherein the antibody is separated from QSOX1 enzyme in the culture; and conjugating the purified antibody via one or more sulfhydryl groups to a cytotoxic drug to produce the conjugated antibody.

13. A method of producing a conjugated antibody, comprising:
(a) performing at least one purification step of a purification scheme to obtain at least a partially purified preparation of an antibody from a culture of CHO cells expressing the antibody;
(b) conjugating the at least partially purified antibody via one or more sulfhydryl groups to a cytotoxic drug under conditions to produce the conjugated antibody; wherein an unacceptably low level of conjugated antibody is produced;
(c) testing the purified preparation of step (a) for presence of a CHO cell sulfhydryl oxidizing enzyme selected from at least one of quiescin Q6 sulfhydryl oxidase 1 (QSOX1), Q6 sulfhydryl oxidase 2 (QSOX2), and Augmenter of Liver Regeneration (ALR);
(d) if the enzyme is detected at a level greater than 0.5 μg/ml or 33 ppm in the preparation of step (c), performing steps (a) and (c) with a different purification step until the enzyme is detected at a level less than 0.5 μg/ml or 33 ppm in the preparation of step (c);
(e) performing the at least one purification step resulting in detection of the enzyme at a level less than 0.5 μg/ml or 33 ppm on a second culture of CHO cells expressing the antibody to obtain purified antibody, wherein the at least one purification step of the purification scheme resulting in detection of the enzyme at a level less than 0.5 μg/ml or 33 ppm comprises at least one of a step of (i) washing a protein A column with a salt wash at a concentration of 150-500 mM NaCl, (ii) performing depth filtration at 230 L/m$^2$/hr and using at least 15 L/m$^2$ of an equilibration buffer with a pH of 7.5-8 and NaCl concentration of 50-100 mM, (iii) using anion exchange with a quaternary ammonium ion column with a buffer having a pH of 7.5-8 and a conductivity of less than or equal to 11 mS/cm, and (iv) performing phenyl membrane filtration using a buffer having a pH of 6-8 and 0.3-0.4M sodium citrate; and
(f) conjugating the purified antibody via one or more sulfhydryl groups to a cytotoxic drug to produce the conjugated antibody.

14. A method of producing a conjugated antibody, comprising:
(a) obtaining a preparation of antibody;
(b) testing the preparation for the presence of a CHO cell sulfhydryl oxidizing enzyme selected from at least one of quiescin Q6 sulfhydryl oxidase 1 (QSOX1), Q6 sulfhydryl oxidase 2 (QSOX2), and Augmenter of Liver Regeneration (ALR);
(c) if the enzyme is detected at a level greater than 0.5 μg/ml or 33 ppm in the preparation of step (b) performing a purification step to remove the enzyme to a level less than 0.5 μg/ml or 33 ppm, wherein the purification step is selected from a step of (i) washing a protein A column with a salt wash at a concentration of 150-500 mM NaCl, (ii) performing depth filtration at 230 L/m$^2$/hr and using at least 15 L/m$^2$ of an equilibration buffer with a pH of 7.5-8 and NaCl concentration of 50-100 mM, (iii) using anion exchange with a quaternary ammonium ion column with a buffer having a pH of 7.5-8 and a conductivity of less than or equal to 11 mS/cm, and (iv) performing phenyl membrane filtration using a buffer having a pH of 6-8 and 0.3-0.4M sodium citrate; and
(d) conjugating the at least partially purified antibody via one or more sulfhydryl groups to a drug to produce the conjugated antibody.

15. The method claim 1, wherein the antibody is an antibody produced in CHO cells.

16. The method claim 1, wherein the antibody preparation has already been subjected to at least one purification step.

17. The method of claim 16 wherein the purification step is a chromatography purification step.

18. The method of claim 1, wherein the testing involves monitoring the reaction between free thiol groups and DTNB in a control sample and a test sample and comparing the two.

19. The method of claim 1, wherein the CHO cell sulfhydryl oxidizing enzyme comprises an amino acid sequence having 90% or higher sequence identity to SEQ ID NO: 2 and retaining sulfhydryl oxidizing ability.

20. The method of claim 1, wherein the CHO cell sulfhydryl oxidizing enzyme comprises an amino acid sequence having amino acids 94 to 571 of SEQ ID NO: 2 and retaining sulfhydryl oxidizing ability.

* * * * *

SEQUENCE LISTING

<160> NUMBER OF SEQ ID NOS: 2

<210> SEQ ID NO 1
<211> LENGTH: 690
<212> TYPE: PRT
<213> ORGANISM: Cricetulus griseus

<400> SEQUENCE: 1

```
Met Ala Thr Gly Leu Arg Arg Arg Glu Tyr Ile Trp Leu Leu Trp Ala
1               5                   10                  15

Leu Thr Ile Thr Val Ser Tyr Leu Val Ala Leu Phe Ser His Leu Leu
            20                  25                  30

Arg Ile Leu Thr Val Lys Lys Leu Gln Trp Arg Pro Val Leu Asn Leu
        35                  40                  45

Ala Val Leu Asp Cys Ala Glu Glu Thr Asn Thr Ala Val Cys Arg Asp
    50                  55                  60

Phe Asn Ile Ser Gly Phe Pro Thr Val Arg Phe Phe Lys Ala Phe Ser
65                  70                  75                  80

Lys Asn Gly Ser Gly Ile Thr Leu Pro Val Ala Asp Ala Ser Val Glu
                85                  90                  95

Thr Leu Arg Arg Lys Leu Ile Asp Ala Leu Glu Ser His Ser Asp Met
            100                 105                 110

Trp Ser Ser Ser Arg Pro Lys Leu Lys Pro Ala Lys Leu Val Glu Ile
        115                 120                 125

Asn Glu Phe Phe Ala Glu Thr Asn Glu Asp Tyr Leu Val Leu Ile Phe
    130                 135                 140

Glu Asp Lys Asp Ser Tyr Val Gly Arg Glu Val Thr Leu Asp Leu Phe
145                 150                 155                 160

Gln His His Ile Pro Val His Arg Val Leu Asn Thr Glu Arg Asn Ala
                165                 170                 175

Val Ser Lys Phe Gly Val Val Glu Phe Pro Ser Cys Tyr Leu Leu Phe
            180                 185                 190

Arg Asn Gly Ser Phe Ser Arg Val Pro Val Val Met Glu Ser Arg Leu
        195                 200                 205
```

```
Phe Tyr Thr Ser Tyr Leu Lys Gly Met Ser Gly Pro Ile Leu Val Asp
    210                 215                 220
Pro Pro Thr Thr Thr Ile Ser Thr Asp Ala Pro Val Thr Thr Asp Val
225                 230                 235                 240
Val Pro Thr Val Trp Lys Val Ala Asn His Ala Arg Ile Tyr Met Ala
                245                 250                 255
Asp Leu Glu Ser Ser Leu His Tyr Ile Phe Leu Val Glu Val Gly Lys
            260                 265                 270
Phe Ser Val Leu Glu Gly Gln Arg Leu Leu Ala Leu Lys Lys Leu Val
        275                 280                 285
Ala Val Leu Ala Lys Tyr Phe Pro Gly Arg Pro Leu Ala Gln Asn Phe
290                 295                 300
Leu His Ser Ile His Asp Trp Leu Gln Arg Gln Arg Lys Lys Ile
305                 310                 315                 320
Pro Tyr Lys Phe Phe Arg Ala Ala Leu Asp Asn Arg Lys Glu Gly Ile
                325                 330                 335
Val Leu Thr Glu Lys Val Asn Trp Val Gly Cys Gln Gly Ser Lys Pro
            340                 345                 350
His Phe Arg Gly Phe Pro Cys Ser Leu Trp Ile Leu Phe His Phe Leu
        355                 360                 365
Thr Val Gln Ala Ser Arg Tyr Ser Glu Asn His Pro Gln Glu Pro Ala
370                 375                 380
Asp Gly Gln Glu Val Leu Gln Ala Met Arg Ser Tyr Val Gln Trp Phe
385                 390                 395                 400
Phe Gly Cys Arg Asp Cys Ala Glu His Phe Glu Asn Met Ala Ala Ser
                405                 410                 415
Thr Met His Arg Val Arg Ser Pro Thr Ser Ala Val Leu Trp Leu Trp
            420                 425                 430
Thr Ser His Asn Lys Val Asn Ala Arg Leu Ser Gly Ala Pro Ser Glu
        435                 440                 445
Asp Pro Tyr Phe Pro Lys Val Gln Trp Pro Leu Arg Glu Leu Cys Phe
450                 455                 460
Asp Cys His Asn Glu Ile Asn Gly Arg Glu Pro Val Trp Asp Leu Glu
465                 470                 475                 480
Ala Thr Tyr Arg Phe Leu Lys Ala His Phe Ser Ser Glu Asn Ile Ile
                485                 490                 495
Leu Asp Thr Pro Val Ala Gly Leu Ala Thr Gln Arg Asn Pro Gln Ile
            500                 505                 510
Leu Gly Ala Thr Pro Glu Pro Val Met Asp Ala Leu Glu Leu Glu Thr
        515                 520                 525
Arg Asn Ser Val Leu Gly His Glu Arg Ala Ala Ser Thr Glu Ser Pro
530                 535                 540
Gly Ala Thr Ala Leu Asn Val Pro Val Gly Lys Pro Glu Ala Ser Gly
545                 550                 555                 560
Pro Gln Ala Leu Tyr Thr Gly Gln Gly Pro Glu His Met Glu Glu
                565                 570                 575
Pro Gln Arg Val Thr Gln Gly His Thr Gln Gly Gln Gln His Leu Ser
            580                 585                 590
Lys Arg Asp Thr Glu Val Leu Thr Leu Pro Glu Val Asn His Leu Gln
        595                 600                 605
Gly Pro Leu Glu Leu Arg Arg Gly Gly Arg Ser Pro Lys Gln Leu Val
610                 615                 620
```

```
Asn Ile Pro Glu Gly Glu Pro Glu Ala Pro Ala Ile Arg Gly Gln Gly
625                 630                 635                 640

Pro Trp Leu Gln Val Leu Gly Arg Gly Phe Ser His Leu Asp Ile Ser
            645                 650                 655

Leu Cys Val Gly Leu Tyr Ser Val Ser Phe Val Cys Leu Leu Ala Met
            660                 665                 670

Tyr Thr Tyr Phe Arg Ala Arg Leu Arg Thr Pro Lys Gly His Leu Val
        675                 680                 685

Thr Gln
    690

<210> SEQ ID NO 2
<211> LENGTH: 571
<212> TYPE: PRT
<213> ORGANISM: Cricetulus griseus

<400> SEQUENCE: 2

Met Arg Arg Cys Gly Arg His Ser Gly Ser Pro Ser Gln Met Leu Leu
1               5                   10                  15

Leu Leu Leu Pro Pro Leu Leu Leu Ala Val Pro Gly Ala Gly Ala Val
            20                  25                  30

Gln Val Ser Val Leu Tyr Ser Ser Asp Pro Val Thr Val Leu Asn
        35                  40                  45

Ala Asn Thr Val Arg Ser Thr Val Leu Arg Ser Asn Gly Ala Trp Ala
    50                  55                  60

Val Glu Phe Phe Ala Ser Trp Cys Gly His Cys Ile Ala Phe Ala Pro
65              70                  75                  80

Thr Trp Lys Glu Leu Ala Tyr Asp Val Arg Glu Trp Arg Pro Val Leu
            85                  90                  95

Asn Leu Ala Val Leu Asp Cys Ala Glu Glu Thr Asn Thr Ala Val Cys
            100                 105                 110

Arg Asp Phe Asn Ile Ser Gly Phe Pro Thr Val Arg Phe Phe Lys Ala
            115                 120                 125

Phe Ser Lys Asn Gly Ser Gly Ile Thr Leu Pro Val Ala Asp Ala Ser
    130                 135                 140

Val Glu Thr Leu Arg Arg Lys Leu Ile Asp Ala Leu Glu Ser His Ser
145                 150                 155                 160

Asp Met Trp Ser Ser Arg Pro Lys Leu Lys Pro Ala Lys Leu Val
            165                 170                 175

Glu Ile Asn Glu Phe Phe Ala Glu Thr Asn Glu Asp Tyr Leu Val Leu
            180                 185                 190

Ile Phe Glu Asp Lys Asp Ser Tyr Val Gly Arg Glu Val Thr Leu Asp
        195                 200                 205

Leu Phe Gln His His Ile Pro Val His Arg Val Leu Asn Thr Glu Arg
    210                 215                 220

Asn Ala Val Ser Lys Phe Gly Val Val Glu Phe Pro Ser Cys Tyr Leu
225                 230                 235                 240

Leu Phe Arg Asn Gly Ser Phe Ser Arg Val Pro Val Val Met Glu Ser
            245                 250                 255

Arg Leu Phe Tyr Thr Ser Tyr Leu Lys Gly Met Ser Gly Pro Ile Leu
            260                 265                 270

Val Asp Pro Pro Thr Thr Thr Ile Ser Thr Asp Ala Pro Val Thr Thr
        275                 280                 285

Asp Val Val Pro Thr Val Trp Lys Val Ala Asn His Ala Arg Ile Tyr
    290                 295                 300
```

-continued

```
Met Ala Asp Leu Glu Ser Ser Leu His Tyr Ile Phe Leu Val Glu Val
305                 310                 315                 320
Gly Lys Phe Ser Val Leu Glu Gly Gln Arg Leu Leu Ala Leu Lys Lys
                325                 330                 335
Leu Val Ala Val Leu Ala Lys Tyr Phe Pro Gly Arg Pro Leu Ala Gln
                340                 345                 350
Asn Phe Leu His Ser Ile His Asp Trp Leu Gln Arg Gln Gln Arg Lys
                355                 360                 365
Lys Ile Pro Tyr Lys Phe Phe Arg Ala Ala Leu Asp Asn Arg Lys Glu
        370                 375                 380
Gly Ile Val Leu Thr Glu Lys Val Asn Trp Val Gly Cys Gln Gly Ser
385                 390                 395                 400
Lys Pro His Phe Arg Gly Phe Pro Cys Ser Leu Trp Ile Leu Phe His
                405                 410                 415
Phe Leu Thr Val Gln Ala Ser Arg Tyr Ser Glu Asn His Pro Gln Glu
                420                 425                 430
Pro Ala Asp Gly Gln Glu Val Leu Gln Ala Met Arg Ser Tyr Val Gln
                435                 440                 445
Trp Phe Phe Gly Cys Arg Asp Cys Ala Glu His Phe Glu Asn Met Ala
        450                 455                 460
Ala Ser Thr Met His Arg Val Arg Ser Pro Thr Ser Ala Val Leu Trp
465                 470                 475                 480
Leu Trp Thr Ser His Asn Lys Val Asn Ala Arg Leu Ser Gly Ala Pro
                485                 490                 495
Ser Glu Asp Pro Tyr Phe Pro Lys Val Gln Trp Pro Leu Arg Glu Leu
                500                 505                 510
Cys Phe Asp Cys His Asn Glu Ile Asn Gly Arg Glu Pro Val Trp Asp
                515                 520                 525
Leu Glu Ala Thr Tyr Arg Phe Leu Lys Ala His Phe Ser Ser Glu Asn
        530                 535                 540
Ile Ile Leu Asp Thr Pro Val Ala Gly Leu Ala Thr Gln Arg Asn Pro
545                 550                 555                 560
Gln Ile Leu Gly Ala Thr Pro Glu Pro His Met
                565                 570
```